United States Patent
Lee et al.

(10) Patent No.: US 9,914,757 B2
(45) Date of Patent: Mar. 13, 2018

(54) METHIONYL TRNA SYNTHETASE FOR BIOSYNTHESIS OF PHOTOMETHIONINE-LABELED PROTEIN AND METHOD FOR PREPARING PHOTOACTIVE PROTEIN G VARIANT USING SAME

(71) Applicant: Korea Research Institute of Bioscience and Biotechnology, Daejeon (KR)

(72) Inventors: Myung Kyu Lee, Daejeon (KR); Bong Hyun Chung, Daejeon (KR); Jeong Hee Moon, Daejeon (KR); Ga Bi Lee, Daejeon (KR)

(73) Assignee: Korean Research Institute of Bioscience and Biotechnology, Daejeon (KR)

( * ) Notice: Subject to any disclaimer, the term of this patent is extended or adjusted under 35 U.S.C. 154(b) by 162 days.

(21) Appl. No.: 14/894,756

(22) PCT Filed: May 29, 2014

(86) PCT No.: PCT/KR2014/004803
§ 371 (c)(1),
(2) Date: Nov. 30, 2015

(87) PCT Pub. No.: WO2014/193176
PCT Pub. Date: Dec. 4, 2014

(65) Prior Publication Data
US 2016/0200777 A1     Jul. 14, 2016

(30) Foreign Application Priority Data

May 30, 2013 (KR) .......................... 10-2013-0061895
Dec. 2, 2013 (KR) .......................... 10-2013-0148287

(51) Int. Cl.
| | | |
|---|---|---|
| C07K 14/315 | (2006.01) | |
| C07K 16/28 | (2006.01) | |
| C12P 21/00 | (2006.01) | |
| C12N 9/00 | (2006.01) | |

(52) U.S. Cl.
CPC ........ C07K 14/315 (2013.01); C07K 16/2863 (2013.01); C12N 9/93 (2013.01); C12P 21/00 (2013.01); C07K 2319/00 (2013.01); C12Y 601/0101 (2013.01)

(58) Field of Classification Search
CPC ........... G01N 2440/00; G01N 33/6848; C12Y 601/0101
See application file for complete search history.

(56) References Cited

FOREIGN PATENT DOCUMENTS

KR     10-2008-0000507 A     1/2008

OTHER PUBLICATIONS

Tanrikulu, I. C. et al., "Discovery of *Escherichia coli* methionyl-tRNA synthetase mutants for efficient labeling of proteins with azidonorleucine in vivo", Proc. Natl. Acad. Sci. USA, Aug. 17, 2009, vol. 106, No. 36, pp. 15285-15290. See abstract; p. 15286, left col.; figures 1-2.

Suchanek, M. et al., "Photo-leucine and photo-methionine allow identification of protein-protein interactions in living cells", Nature Methods, Mar. 23, 2005, vol. 2, No. 4, pp. 261-267. See abstract; pp. 261-262; figures 1-2.

Crepin, T. et al., "Use of analogues of methionine and methionyl adenylate to sample conformational changes during catalysis in *Escherichia coli* methionyl-tRNA synthetase," J. Mol. Biol., Sep. 5, 2003, vol. 332, No. 1, pp. 59-72. See abstract; figures 2-6.

Hino, N. et al., "Protein photo-cross-linking in mammalian cells by site-specific incorporation of a photoreactive amino acid", Nature Methods, Feb. 17, 2005, vol. 2, No. 3, pp. 201-206. See abstract; figure 1.

International Search Report dated Sep. 22, 2014 (PCT/KR2014/004803); ISA/KR.

*Primary Examiner* — Kagnew H Gebreyesus
(74) *Attorney, Agent, or Firm* — Banner & Witcoff, Ltd.

(57) ABSTRACT

Provided is a methionyl tRNA synthase (MRS) for the biosynthesis of a photomethionine-labeled protein and a method for preparing a photoactivatable protein G variant using same and, more particularly, to an MRS variant in which alanine at the position of $12^{th}$ is substituted with glycine, leucine at the position of $13^{th}$ by serine, tyrosine at the position of $260^{th}$ by phenylalanine, isoleucine at the position of $297^{th}$ by valine, and histidine at the position of $301^{st}$ by leucine from the N-terminal of the amino acid sequence of a wild-type *Escherichia coli* methionyl tRNA synthase. The MRS variant effectively confirms the biosynthesis of a photomethionine (pM)-labeled target protein and thus can be utilized for the biosynthesis of a pM-labeled target protein. In addition, a pM-introduced protein G variant, in which a plasmid encoding the MRS variant (MRS5m) and a PG-C3 plasmid, in which, in the third immunoglobulin G binding region of protein G, positions of $32^{nd}$, $35^{th}$, and $40^{th}$ are substituted with a methionine (Met) residue and a position of $37^{th}$ by an arginine (Arg) residue, are introduced into *Escherichia coli* and then refined, has a specific covalent bond with an antibody when subject to UV irradiation, and thus the pM-introduced protein G variant using the MRS variant can be utilized for producing a highly sensitive biochip, biosensor, or cell-capturing chip.

15 Claims, 22 Drawing Sheets

Protein G C1-C3 domains (Olsson et al., Eur J Biochem, 168, 319-24, 1987)

PG-C1 : TYKLILNGKTLKGETTTEAVDAATAEKVFKQYANDNGVDGEWTYDDATKTFTVTE

PG-C2 : TYKLVINGKTLKGETTTEAVDAATAEKVFKQYANDNGVDGEWTYDDATKTFTVTE

PG-C3 : TYKLVINGKTLKGETTTKAVDAETAEKAFKQYANDNGVDGVWTYDDATKTFTVTE

SEQUENCE LISTING

```
<160> NUMBER OF SEQ ID NOS: 43

<210> SEQ ID NO 1
<211> LENGTH: 677
<212> TYPE: PRT
<213> ORGANISM: E. coli

<400> SEQUENCE: 1

Met Thr Gln Val Ala Lys Lys Ile Leu Val Thr Cys Ala Leu Pro Tyr
 1               5                  10                  15

Ala Asn Gly Ser Ile His Leu Gly His Met Leu Glu His Ile Gln Ala
                20                  25                  30

Asp Val Trp Val Arg Tyr Gln Arg Met Arg Gly His Glu Val Asn Phe
            35                  40                  45

Ile Cys Ala Asp Asp Ala His Gly Thr Pro Ile Met Leu Lys Ala Gln
        50                  55                  60

Gln Leu Gly Ile Thr Pro Glu Gln Met Ile Gly Glu Met Ser Gln Glu
    65                  70                  75                  80

His Gln Thr Asp Phe Ala Gly Phe Asn Ile Ser Tyr Asp Asn Tyr His
                85                  90                  95

Ser Thr His Ser Glu Glu Asn Arg Gln Leu Ser Glu Leu Ile Tyr Ser
            100                 105                 110

Arg Leu Lys Glu Asn Gly Phe Ile Lys Asn Arg Thr Ile Ser Gln Leu
        115                 120                 125

Tyr Asp Pro Glu Lys Gly Met Phe Leu Pro Asp Arg Phe Val Lys Gly
    130                 135                 140
```

-continued

```
Thr Cys Pro Lys Cys Lys Ser Pro Asp Gln Tyr Gly Asp Asn Cys Glu
145                 150                 155                 160

Val Cys Gly Ala Thr Tyr Ser Pro Thr Glu Leu Ile Glu Pro Lys Ser
                165                 170                 175

Val Val Ser Gly Ala Thr Pro Val Met Arg Asp Ser Glu His Phe Phe
            180                 185                 190

Phe Asp Leu Pro Ser Phe Ser Glu Met Leu Gln Ala Trp Thr Arg Ser
        195                 200                 205

Gly Ala Leu Gln Glu Gln Val Ala Asn Lys Met Gln Glu Trp Phe Glu
    210                 215                 220

Ser Gly Leu Gln Gln Trp Asp Ile Ser Arg Asp Ala Pro Tyr Phe Gly
225                 230                 235                 240

Phe Glu Ile Pro Asn Ala Pro Gly Lys Tyr Phe Tyr Val Trp Leu Asp
                245                 250                 255

Ala Pro Ile Gly Tyr Met Gly Ser Phe Lys Asn Leu Cys Asp Lys Arg
            260                 265                 270

Gly Asp Ser Val Ser Phe Asp Glu Tyr Trp Lys Lys Asp Ser Thr Ala
        275                 280                 285

Glu Leu Tyr His Phe Ile Gly Lys Asp Ile Val Tyr Phe His Ser Leu
    290                 295                 300

Phe Trp Pro Ala Met Leu Glu Gly Ser Asn Phe Arg Lys Pro Ser Asn
305                 310                 315                 320

Leu Phe Val His Gly Tyr Val Thr Val Asn Gly Ala Lys Met Ser Lys
                325                 330                 335

Ser Arg Gly Thr Phe Ile Lys Ala Ser Thr Trp Leu Asn His Phe Asp
            340                 345                 350

Ala Asp Ser Leu Arg Tyr Tyr Tyr Thr Ala Lys Leu Ser Ser Arg Ile
        355                 360                 365

Asp Asp Ile Asp Leu Asn Leu Glu Asp Phe Val Gln Arg Val Asn Ala
    370                 375                 380

Asp Ile Val Asn Lys Val Val Asn Leu Ala Ser Arg Asn Ala Gly Phe
385                 390                 395                 400

Ile Asn Lys Arg Phe Asp Gly Val Leu Ala Ser Glu Leu Ala Asp Pro
                405                 410                 415

Gln Leu Tyr Lys Thr Phe Thr Asp Ala Ala Glu Val Ile Gly Glu Ala
            420                 425                 430

Trp Glu Ser Arg Glu Phe Gly Lys Ala Val Arg Glu Ile Met Ala Leu
        435                 440                 445

Ala Asp Leu Ala Asn Arg Tyr Val Asp Glu Gln Ala Pro Trp Val Val
    450                 455                 460

Ala Lys Gln Glu Gly Arg Asp Ala Asp Leu Gln Ala Ile Cys Ser Met
465                 470                 475                 480

Gly Ile Asn Leu Phe Arg Val Leu Met Thr Tyr Leu Lys Pro Val Leu
                485                 490                 495

Pro Lys Leu Thr Glu Arg Ala Glu Ala Phe Leu Asn Thr Glu Leu Thr
            500                 505                 510

Trp Asp Gly Ile Gln Gln Pro Leu Leu Gly His Lys Val Asn Pro Phe
        515                 520                 525

Lys Ala Leu Tyr Asn Arg Ile Asp Met Arg Gln Val Glu Ala Leu Val
    530                 535                 540

Glu Ala Ser Lys Glu Glu Val Lys Ala Ala Ala Pro Val Thr Gly
545                 550                 555                 560
```

```
Pro Leu Ala Asp Asp Pro Ile Gln Glu Thr Ile Thr Phe Asp Asp Phe
                565                 570                 575
Ala Lys Val Asp Leu Arg Val Ala Leu Ile Glu Asn Ala Glu Phe Val
            580                 585                 590
Glu Gly Ser Asp Lys Leu Leu Arg Leu Thr Leu Asp Leu Gly Gly Glu
        595                 600                 605
Lys Arg Asn Val Phe Ser Gly Ile Arg Ser Ala Tyr Pro Asp Pro Gln
    610                 615                 620
Ala Leu Ile Gly Arg His Thr Ile Met Val Ala Asn Leu Ala Pro Arg
625                 630                 635                 640
Lys Met Arg Phe Gly Ile Ser Glu Gly Met Val Met Ala Ala Gly Pro
                645                 650                 655
Gly Gly Lys Asp Ile Phe Leu Leu Ser Pro Asp Ala Gly Ala Lys Pro
            660                 665                 670
Gly His Gln Val Lys
        675

<210> SEQ ID NO 2
<211> LENGTH: 55
<212> TYPE: PRT
<213> ORGANISM: Homo sapiens

<400> SEQUENCE: 2

Thr Tyr Lys Leu Ile Leu Asn Gly Lys Thr Leu Lys Gly Glu Thr Thr
1               5                   10                  15
Thr Glu Ala Val Asp Ala Ala Thr Ala Glu Lys Val Phe Lys Gln Tyr
            20                  25                  30
Ala Asn Asp Asn Gly Val Asp Gly Glu Trp Thr Tyr Asp Asp Ala Thr
        35                  40                  45
Lys Thr Phe Thr Val Thr Glu
    50                  55

<210> SEQ ID NO 3
<211> LENGTH: 55
<212> TYPE: PRT
<213> ORGANISM: Homo sapiens

<400> SEQUENCE: 3

Thr Tyr Lys Leu Val Ile Asn Gly Lys Thr Leu Lys Gly Glu Thr Thr
1               5                   10                  15
Thr Glu Ala Val Asp Ala Ala Thr Ala Glu Lys Val Phe Lys Gln Tyr
            20                  25                  30
Ala Asn Asp Asn Gly Val Asp Gly Glu Trp Thr Tyr Asp Asp Ala Thr
        35                  40                  45
Lys Thr Phe Thr Val Thr Glu
    50                  55

<210> SEQ ID NO 4
<211> LENGTH: 55
<212> TYPE: PRT
<213> ORGANISM: Homo sapiens

<400> SEQUENCE: 4

Thr Tyr Lys Leu Val Ile Asn Gly Lys Thr Leu Lys Gly Glu Thr Thr
1               5                   10                  15
Thr Lys Ala Val Asp Ala Glu Thr Ala Glu Lys Ala Phe Lys Gln Tyr
            20                  25                  30
Ala Asn Asp Asn Gly Val Asp Gly Val Trp Thr Tyr Asp Asp Ala Thr
```

```
            35                  40                  45
Lys Thr Phe Thr Val Thr Glu
  50                  55

<210> SEQ ID NO 5
<211> LENGTH: 2034
<212> TYPE: DNA
<213> ORGANISM: E. coli

<400> SEQUENCE: 5
atgactcaag tcgcgaagaa aattctggtg acgtgcgcac tgccgtacgc taacggctca     60
atccacctcg gccatatgct ggagcacatc caggctgatg tctgggtccg ttaccagcga    120
atgcgcggcc acgaggtcaa cttcatctgc gccgacgatg cccacggtac accgatcatg    180
ctgaaagctc agcagcttgg tatcaccccg agcagatga ttggcgaaat gagtcaggag     240
catcagactg atttcgcagg ctttaacatc agctatgaca actatcactc gacgcacagc    300
gaagagaacc gccagttgtc agaacttatc tactctcgcc tgaaagaaaa cggttttatt    360
aaaaaccgca ccatctctca gctgtacgat ccggaaaaag gcatgttcct gccggaccgt    420
tttgtgaaag gcacctgccc gaaatgtaaa tccccggatc aatacggcga taactgcgaa    480
gtctgcggcg cgacctacag cccgactgaa ctgatcgagc cgaaatcggt ggtttctggc    540
gctacgccgg taatgcgtga ttctgaacac ttcttctttg atctgccctc tttcagcgaa    600
atgttgcagg catggacccg cagcggtgcg ttgcaggagc aggtggcaaa taaaatgcag    660
gagtggtttg aatctggcct gcaacagtgg gatatctccc gcgacgcccc ttacttcggt    720
tttgaaattc cgaacgcgcc gggcaaatat ttctacgtct ggctggacgc accgattggc    780
tacatgggtt ctttcaagaa tctgtgcgac aagcgcggcg acagcgtaag cttcgatgaa    840
tactggaaga aagactccac cgccgagctg taccacttca tcggtaaaga tattgtttac    900
ttccacagcc tgttctggcc tgccatgctg gaaggcagca acttccgcaa gccgtccaac    960
ctgtttgttc atggctatgt gacggtgaac ggcgcaaaga tgtccaagtc tcgcggcacc   1020
tttattaaag ccagcacctg gctgaatcat tttgacgcag acagcctgcg ttactactac    1080
actgcgaaac tctcttcgcg cattgatgat atcgatctca acctggaaga tttcgttcag   1140
cgtgtgaatg ccgatatcgt taacaaagtg gttaacctgg cctcccgtaa tgcgggcttt   1200
atcaacaagc gttttgacgg cgtgctggca agcgaactgc tgacccgca gttgtacaaa     1260
accttcactg atgccgctga agtgattggt gaagcgtggg aaagccgtga atttggtaaa   1320
gccgtgcgcg aaatcatggc gctggctgat ctggctaacc gctatgtcga tgaacaggct    1380
ccgtgggtgg tggcgaaaca ggaaggccgc gatgccgacc tgcaggcaat tgctcaatg    1440
ggcatcaacc tgttccgcgt gctgatgact tacctgaagc cggtactgcc gaaactgacc    1500
gagcgtgcag aagcattcct caatacggaa ctgacctggg atggtatcca gcaaccgctg    1560
ctgggccaca agtgaatcc gttcaaggcg ctgtataacc gcatcgatat gaggcaggtt     1620
gaagcactgg tggaagcctc taagaagaa gtaaaagccg ctgccgcgcc ggtaactggc     1680
ccgctggcag atgatccgat tcaggaaacc atcaccttg acgacttcgc taaagttgac    1740
ctgcgcgtgc cgctgattga aaacgcagag tttgttgaag ttctgacaa actgctgcgc     1800
ctgacgctgg atctcggcgg tgaaaaacgc aatgtcttct ccggtattcg ttctgcttac    1860
ccggatccgc aggcactgat tggtcgtcac accattatgg tggctaacct ggcaccacgt    1920
aaaatgcgct tcggtatctc tgaaggcatg gtgatggctg ccggtcctgg cgggaaagat   1980
```

```
attttcctgc taagcccgga tgccggtgct aaaccgggtc atcaggtgaa ataa        2034
```

<210> SEQ ID NO 6
<211> LENGTH: 28
<212> TYPE: DNA
<213> ORGANISM: Artificial Sequence
<220> FEATURE:
<223> OTHER INFORMATION: TET-Xba-F

<400> SEQUENCE: 6

```
ttcccctcta gaaataattt tgtttaac                                     28
```

<210> SEQ ID NO 7
<211> LENGTH: 27
<212> TYPE: DNA
<213> ORGANISM: Artificial Sequence
<220> FEATURE:
<223> OTHER INFORMATION: ET-Bam-R

<400> SEQUENCE: 7

```
gcgcggatcc gcgcggcacc aggccgc                                      27
```

<210> SEQ ID NO 8
<211> LENGTH: 26
<212> TYPE: DNA
<213> ORGANISM: Artificial Sequence
<220> FEATURE:
<223> OTHER INFORMATION: GFP-Bam-F

<400> SEQUENCE: 8

```
cgggatccat ggtgagcaag ggcgag                                       26
```

<210> SEQ ID NO 9
<211> LENGTH: 27
<212> TYPE: DNA
<213> ORGANISM: Artificial Sequence
<220> FEATURE:
<223> OTHER INFORMATION: GFP-Xho-R

<400> SEQUENCE: 9

```
ccgctcgagt tacttgtaca gctcgtc                                      27
```

<210> SEQ ID NO 10
<211> LENGTH: 28
<212> TYPE: DNA
<213> ORGANISM: Artificial Sequence
<220> FEATURE:
<223> OTHER INFORMATION: GFP-FIH-R

<400> SEQUENCE: 10

```
cgccgctgtc ccgccgagag tgatcccg                                     28
```

<210> SEQ ID NO 11
<211> LENGTH: 28
<212> TYPE: DNA
<213> ORGANISM: Artificial Sequence
<220> FEATURE:
<223> OTHER INFORMATION: GFP-FIH-F

<400> SEQUENCE: 11

```
actctcggcg ggacagcggc ggaggctg                                     28
```

<210> SEQ ID NO 12
<211> LENGTH: 26
<212> TYPE: DNA
<213> ORGANISM: Artificial Sequence

```
<220> FEATURE:
<223> OTHER INFORMATION: GFP-Xho-R

<400> SEQUENCE: 12
ttccctcgag acccctggca ggctag                                         26

<210> SEQ ID NO 13
<211> LENGTH: 23
<212> TYPE: DNA
<213> ORGANISM: Artificial Sequence
<220> FEATURE:
<223> OTHER INFORMATION: MRS-Nco-F

<400> SEQUENCE: 13
aattccatgg ctcaagtcgc gaa                                            23

<210> SEQ ID NO 14
<211> LENGTH: 32
<212> TYPE: DNA
<213> ORGANISM: Artificial Sequence
<220> FEATURE:
<223> OTHER INFORMATION: MRS-Kpn-R

<400> SEQUENCE: 14
cagcggtacc ttattcttta gaggcttcca cc                                  32

<210> SEQ ID NO 15
<211> LENGTH: 21
<212> TYPE: DNA
<213> ORGANISM: Artificial Sequence
<220> FEATURE:
<223> OTHER INFORMATION: BAD-F

<400> SEQUENCE: 15
atgccatagc atttttatcc a                                              21

<210> SEQ ID NO 16
<211> LENGTH: 35
<212> TYPE: DNA
<213> ORGANISM: Artificial Sequence
<220> FEATURE:
<223> OTHER INFORMATION: MRS-A12G-F

<400> SEQUENCE: 16
gacgtgcggc ctgccgtacg ctaacggctc aatcc                               35

<210> SEQ ID NO 17
<211> LENGTH: 31
<212> TYPE: DNA
<213> ORGANISM: Artificial Sequence
<220> FEATURE:
<223> OTHER INFORMATION: MRS-A12G-R

<400> SEQUENCE: 17
acggcaggcc gcacgtcacc agaattttct t                                   31

<210> SEQ ID NO 18
<211> LENGTH: 24
<212> TYPE: DNA
<213> ORGANISM: Artificial Sequence
<220> FEATURE:
<223> OTHER INFORMATION: MRS-L13G-F

<400> SEQUENCE: 18
gggccgtacg ctaacggctc aatc                                           24
```

<210> SEQ ID NO 19
<211> LENGTH: 39
<212> TYPE: DNA
<213> ORGANISM: Artificial Sequence
<220> FEATURE:
<223> OTHER INFORMATION: MRS-L13G-R

<400> SEQUENCE: 19
gattgagccg ttagcgtacg gccctgcgca cgtcaccag          39

<210> SEQ ID NO 20
<211> LENGTH: 34
<212> TYPE: DNA
<213> ORGANISM: Artificial Sequence
<220> FEATURE:
<223> OTHER INFORMATION: MRS-AL/GS-F

<400> SEQUENCE: 20
gacgtgcggc tcgccgtacg ctaacggctc aatc               34

<210> SEQ ID NO 21
<211> LENGTH: 34
<212> TYPE: DNA
<213> ORGANISM: Artificial Sequence
<220> FEATURE:
<223> OTHER INFORMATION: MRS-AL/GS-R

<400> SEQUENCE: 21
acggcgagcc gcacgtcacc agaattttct tcgc               34

<210> SEQ ID NO 22
<211> LENGTH: 39
<212> TYPE: DNA
<213> ORGANISM: Artificial Sequence
<220> FEATURE:
<223> OTHER INFORMATION: MRS-Y260F-F

<400> SEQUENCE: 22
accgattggc ttcatgggtt ctttcaagaa tctgtgcga          39

<210> SEQ ID NO 23
<211> LENGTH: 32
<212> TYPE: DNA
<213> ORGANISM: Artificial Sequence
<220> FEATURE:
<223> OTHER INFORMATION: MRS-Y260F-R

<400> SEQUENCE: 23
aagaacccat gaagccaatc ggtgcgtcca gc                 32

<210> SEQ ID NO 24
<211> LENGTH: 38
<212> TYPE: DNA
<213> ORGANISM: Artificial Sequence
<220> FEATURE:
<223> OTHER INFORMATION: MRS-I297V-F

<400> SEQUENCE: 24
ggtaaagatg ttgtttactt cctgagcctg ttctggcc           38

<210> SEQ ID NO 25
<211> LENGTH: 43
<212> TYPE: DNA
<213> ORGANISM: Artificial Sequence
<220> FEATURE:
<223> OTHER INFORMATION: MRS-I297V-R

<400> SEQUENCE: 25
ggctcaggaa gtaaacaaca tctttaccga tgaagtggta cag                    43

<210> SEQ ID NO 26
<211> LENGTH: 35
<212> TYPE: DNA
<213> ORGANISM: Artificial Sequence
<220> FEATURE:
<223> OTHER INFORMATION: MRS-H301L-F

<400> SEQUENCE: 26
gatattgttt acttcctgag cctgttctgg cctgc                             35

<210> SEQ ID NO 27
<211> LENGTH: 35
<212> TYPE: DNA
<213> ORGANISM: Artificial Sequence
<220> FEATURE:
<223> OTHER INFORMATION: MRS-H301L-R

<400> SEQUENCE: 27
cagaacaggc tcaggaagta aacaatatct ttacc                             35

<210> SEQ ID NO 28
<211> LENGTH: 42
<212> TYPE: DNA
<213> ORGANISM: Artificial Sequence
<220> FEATURE:
<223> OTHER INFORMATION: PG-Bam-F forward primer

<400> SEQUENCE: 28
ataggatcct gctgcggcgg gacaacttac aaacttgtta tt                     42

<210> SEQ ID NO 29
<211> LENGTH: 32
<212> TYPE: DNA
<213> ORGANISM: Artificial Sequence
<220> FEATURE:
<223> OTHER INFORMATION: PG-Xho-R reverse primer

<400> SEQUENCE: 29
gcgcctcgag ttattcagtt accgtaaagg tc                                32

<210> SEQ ID NO 30
<211> LENGTH: 42
<212> TYPE: DNA
<213> ORGANISM: Artificial Sequence
<220> FEATURE:
<223> OTHER INFORMATION: PG-Bam-F

<400> SEQUENCE: 30
ataggatcct gctgcggcgg gacaacttac aaacttgtta tt                     42

<210> SEQ ID NO 31
<211> LENGTH: 32
<212> TYPE: DNA
<213> ORGANISM: Artificial Sequence
<220> FEATURE:
<223> OTHER INFORMATION: PG-XhoI-R

<400> SEQUENCE: 31
gcgcctcgag ttattcagtt accgtaaagg tc                                32

<210> SEQ ID NO 32

```
<211> LENGTH: 32
<212> TYPE: DNA
<213> ORGANISM: Artificial Sequence
<220> FEATURE:
<223> OTHER INFORMATION: PG-Q32M-F

<400> SEQUENCE: 32
aaagccttca aaatgtacgc taacgagaac gg                                    32

<210> SEQ ID NO 33
<211> LENGTH: 39
<212> TYPE: DNA
<213> ORGANISM: Artificial Sequence
<220> FEATURE:
<223> OTHER INFORMATION: PG-Q32M-R

<400> SEQUENCE: 33
gttagcgtac attttgaagg cttttctgc agtttctgc                              39

<210> SEQ ID NO 34
<211> LENGTH: 34
<212> TYPE: DNA
<213> ORGANISM: Artificial Sequence
<220> FEATURE:
<223> OTHER INFORMATION: PG-D40M-F

<400> SEQUENCE: 34
gacaacggtg ttatgggtgt ttggacttat gatg                                  34

<210> SEQ ID NO 35
<211> LENGTH: 31
<212> TYPE: DNA
<213> ORGANISM: Artificial Sequence
<220> FEATURE:
<223> OTHER INFORMATION: PG-D40M-R

<400> SEQUENCE: 35
ccaaacaccc ataacaccgt tgtcgttagc g                                     31

<210> SEQ ID NO 36
<211> LENGTH: 30
<212> TYPE: DNA
<213> ORGANISM: Artificial Sequence
<220> FEATURE:
<223> OTHER INFORMATION: PG-N37R-F

<400> SEQUENCE: 36
gctaacgacc gcggtgttat gggtgtttgg                                       30

<210> SEQ ID NO 37
<211> LENGTH: 30
<212> TYPE: DNA
<213> ORGANISM: Artificial Sequence
<220> FEATURE:
<223> OTHER INFORMATION: PG-N37R-R

<400> SEQUENCE: 37
cataacaccg cggtcgttag cgtacatttt                                       30

<210> SEQ ID NO 38
<211> LENGTH: 30
<212> TYPE: DNA
```

<213> ORGANISM: Artificial Sequence
<220> FEATURE:
<223> OTHER INFORMATION: PG-35, 37-F

<400> SEQUENCE: 38
gctatggacc gcggtgttat gggtgtttgg                                    30

<210> SEQ ID NO 39
<211> LENGTH: 36
<212> TYPE: DNA
<213> ORGANISM: Artificial Sequence
<220> FEATURE:
<223> OTHER INFORMATION: PG-35, 37-R

<400> SEQUENCE: 39
cataacaccg cggtccatag cgtacatttt gaaggc                             36

<210> SEQ ID NO 40
<211> LENGTH: 24
<212> TYPE: DNA
<213> ORGANISM: Artificial Sequence
<220> FEATURE:
<223> OTHER INFORMATION: Ins-Cla-F

<400> SEQUENCE: 40
gaagtgatcg atgcgtctga atta                                          24

<210> SEQ ID NO 41
<211> LENGTH: 24
<212> TYPE: DNA
<213> ORGANISM: Artificial Sequence
<220> FEATURE:
<223> OTHER INFORMATION: Ins-Cla-R

<400> SEQUENCE: 41
taattcagac gcatcgatca cttc                                          24

<210> SEQ ID NO 42
<211> LENGTH: 28
<212> TYPE: DNA
<213> ORGANISM: Artificial Sequence
<220> FEATURE:
<223> OTHER INFORMATION: ET-Xba-F

<400> SEQUENCE: 42 ttccctcta gaaataattt tgtttaac                                       28

<210> SEQ ID NO 43
<211> LENGTH: 29
<212> TYPE: DNA
<213> ORGANISM: Artificial Sequence
<220> FEATURE:
<223> OTHER INFORMATION: ET-R

<400> SEQUENCE: 43
ttatgctagt tattgctcag cggtggcag                                     29

METHIONYL TRNA SYNTHETASE FOR BIOSYNTHESIS OF PHOTOMETHIONINE-LABELED PROTEIN AND METHOD FOR PREPARING PHOTOACTIVE PROTEIN G VARIANT USING SAME

TECHNICAL FIELD

The present invention relates to a methionyl tRNA synthetase (MRS) for introducing photomethionine (pM) to a target protein in vivo and a method for preparing pM-introduced protein G variants which are able to induce covalent photocrosslinking with antibodies upon ultraviolet (UV) irradiation.

BACKGROUND ART

Formation of covalent bonds between biopolymers by photoactivity plays an important role in researches of their structures and functions by providing important information to interaction between the molecules. The method is used as a tool for analyzing protein-protein interactions (Suchanek et. al., Nat Methods, 2, 261-7, 2005; Chou et. al., Chem Sci, 2, 480-83, 2011), protein-lipid interactions (Gubbens et. al., Chem Biol, 16, 3-14, 2009), protein-nucleic acid interactions (Pingoud et. al., Mol Biosyst, 1, 135-41, 2005), and the like.

Chemical conjugation of a photoactivatable group such as diazirine, benzophenone, and azide groups, to lysine residues of a protein has some disadvantages such as increase of hydrophobicity, interference of specific binding and increase of nonspecific binding.

In order to compensate such disadvantages, Jung introduced cysteine residues at specific positions of protein G and a photoactivatable group introduced to the cysteine residues of the protein G (Jung et. al., Anal Chem, 81, 936-42, 2009).

Studies to introduce nonnatural amino acids (NAAs) into proteins using in-vivo protein biosynthesis processes have been conducted (Davis and Chin, Nat Reviews Mol Cell Biol, 13, 168-182, 2012). Dr. Schulz's team in the US Scripps research institute conducted many studies in which in the natural world to introduce a NAA into the specific position of a protein by utilizing an amino acyl tRNA$_{CUA}$ synthase and a tRNA$_{CUA}$ pair recognizing TAG which is an amber stop codon, and thus, successfully, introduced various NAAs into proteins using in-vivo translation systems (Xie and Schulz, Nat Reviews Mol Cell Biol, 7, 775-82, 2006). Professor Tirrell's team of CALTECH in USA studied introduction of a NAA by preparing a methionyl tRNA synthase (MRS) variant. Particularly, azidonorleucine was successfully introduced into the methionine residues of dihydrofolate reductase of E. coli by inducing variants at Leu13, Tyr260, His301 sites (Crepin et. al., J Mol Biol, 332, 59-72, 2003) known as binding regions of the methionine of the MRS (Tanrikulu et. al., Proc Nat Acad Sci USA, 106, 15285-90, 2009).

Studies to introduce photoactivatable NAAs into proteins in the protein biosynthesis step in vivo have been conducted. Tippmann et. al. successfully introduced 4'-[3-(trifluoromethyl)-3H-diazin-3-yl]-1-phenylalanine (TfmdPhe) into a Z-domain protein in E. coli by using an amino acid tRNA$_{CUA}$ synthase/tRNA$_{CUA}$ system (Tippmann et. al., ChemBioChem, 8, 2210-14, 2007). Further, it was verified that lysine introduced with a diazirine group was successfully introduced into a target protein in E. coli and animal cell by using a pyrrolysyl (Pyl) tRNA$_{CUA}$ synthase/Pyl-tRNA$_{CUA}$ system and a covalent bond between proteins by photoactivity may be induced (Chou et. al., Chem Sci, 2, 480-83, 2011). However, the residues have bulky and long carbon chains and thus, have a disadvantage of delicately forming a covalent bond with the target molecule. Such problems can be solved by using photoleucine (pL; L-2-amino-4,4-azi-pentanoic acid) or photomethionine (pM; L-2-amino-5,5-azi-hexanoic acid) which is very similar to leucine or methionine. Suchanek et. al. (Nat Methods, 2, 261-7, 2005) utilized the photoactivatable amino acid mimetic labeled in the protein in analysis of the bond between proteins after biosynthesizing the protein by adding the pM or pL photoactivatable amino acid mimetics in a medium without methionine or leucine in an animal cell culture. However, the inventors found very low protein expression in a minimal medium supplemented with pM instate of methionine in methionine-auxotroph E. coli B834 cells.

Since the antibody is very specifically bound with the antigen, the antibody has been used widely in medical researches associated with diagnosis and treatment of diseases and analyzing biological materials (Curr. Opin. Biotechnol. 12 (2001) 65-69, Curr. Opin. Chem. Biol. 5(2001) 40-45). Recently, as one immunological measurement method, a immunosensor of immobilizing the antibody to a solid support material and measuring current, resistance, a change in mass, an optical characteristic, and the like has been developed (affinity biosensors. vol. 7: Techniques and protocols). The immunosensor based on surface plasmon resonance using the optical characteristic has been commercialized, and a biosensor based on the surface plasmon resonance may provide qualitative information (whether two molecules are specifically bound with each other) and quantitative information (reaction kinetics and equilibrium constants) and detect them in real time without labeling and thus is particularly utilized for measuring binding of the antigen and the antibody (J. Mol. Recognit. 1999, 12, 390-408).

In an immunosensor, it is very important to selectively and stably immobilize the antibody to the solid support material. A technology of immobilizing the antibody largely includes a chemical immobilizing method and a physical immobilizing method. The physical method (Trends Anal. Chem. 2000, 19, 530-540) is almost not used due to low reproducibility and modification of the protein and the chemical method (Langumur, 1997, 13, 6485-6490) has been frequently used because the proteins are bound with each other well with a covalent bond to have good reproducibility and a wide application range. However, when immobilizing the antibody by the chemical method, the antibody is an asymmetrical macromolecule and thus the antibody loses orientation or loses activity of biding the antibody (Analyst, 1996, 121(3): 29R-32R).

In order to improve the antigen binding ability of the antibody, a supporter may be used before binding the antibody with the solid support material and a technology using the protein G as the supporter has been known.

The protein G as a protein of strong binding with most mammalian immunoglobulin G (IgG) Fc site is much utilized for preparing a highly sensitive chip with improved orientation of the antibody when preparing the antibody chip. Further, the protein G is bound with nanoparticles and the like and bound with the antibody to be utilized for preparing a target-oriented delivery system. However, since the binding of the protein G and the antibody is reversible, in the case of using a blood sample, the blood sample may be replaced with the antibody in the blood (Saleemuddin, Adv Biochem Eng Biotechnol, 64, 203-26, 1999), and thus it is important to form the covalent bond therebetween. The covalent bond between the molecules may be chemically induced, but has a disadvantage of causing a non-specific conjugation between the molecules.

Accordingly, the inventors made an effort to improve introduction of photomethionine (pM) in the biosynthesized protein and develop the protein G variant with improved antibody-specific to successfully prepare an *E. coli* methionyl tRNA synthase (MRS) variant capable of improving expression of a pM-introduced target protein in *E. coli*. Further, the plasmid encoding the MRS5m which is the MRS variant and the PG-C3 plasmid in which the positions of $32^{nd}$, $35^{th}$, and $40^{th}$ of the third immunoglobulin G binding region C3 (PG-C3) of the protein G were substituted by Met residues and a position of $37^{th}$ was substituted by an Arg residue were introduced into *E. coli* and purified to obtain the photoactivatable mimetic-introduced protein G variant, the specific covalent bond was formed by irradiating UV to the protein G variant and the antibody, and thus the photoactivatable methionine mimetic-introduced protein G variant may be utilized for preparing a highly sensitive biochip, a biosensor, and a cell-capturing chip, thereby completing the present invention.

DISCLOSURE

Technical Problem

An object of the present invention is to provide a methionyl tRNA synthase (MRS) variant for introducing photomethionine (pM) to a target protein in vivo.

Another object of the present invention is to provide a protein G variant constituted by an amino acid sequence in which glutamine (Gln) at the position of $32^{nd}$, asparagine (Asn) at the position of $35^{th}$, or aspartic acid (Asp) at the position of $40^{th}$ is substituted with methionine (Met) or asparagine (Asn) at the position of $37^{th}$ is substituted with arginine (Arg) from an N-terminal of any one amino acid sequence which is selected from a group comprised of a first immunoglobulin G binding region C1 (PG-C1), a second immunoglobulin G binding region C2 (PG-C2), and a third immunoglobulin G binding region C3 (PG-C3) of a protein G, a protein G variant having photoactivity which introduces pM to the protein G variant, and a method for preparing the same.

Technical Solution

One aspect of the present invention provides an methionyl tRNA synthase (MRS) variant for introducing photomethionine (pM) to a target protein constituted by an amino sequence in which alanine at the position of $12^{th}$ is substituted with glycine, leucine at the position of $13^{th}$ by serine, tyrosine at the position of $260^{th}$ by phenylalanine, isoleucine at the position of $297^{th}$ by valine, and histidine at the position of $301^{st}$ by leucine from an N-terminal of an amino acid sequence of a wild-type *Escherichia coli* methionyl tRNA synthase, and a method for preparing the same.

Further, another aspect of the present invention provides a reagent composition for introducing pM to a target protein comprising the MRS variant.

Further, yet another aspect of the present invention provides a method for introducing pM to a target protein comprising:

1) preparing an expression vector including polynucleotide encoding the target protein and an expression vector including polynucleotide encoding the MRS variant;

2) preparing a transformant by simultaneously introducing the expression vectors of the step 1) into *Escherichia coli*; and 3) expressing the pM-labeled target protein by culturing the transformant of the step 2).

Further, still another object of the present invention provides a protein G variant constituted by an amino acid sequence in which glutamine (Gln) at the position of $32^{nd}$, asparagine (Asn) at the position of $35^{th}$, or aspartic acid (Asp) at the position of $40^{th}$ is substituted with methionine (Met) or asparagine (Asn) at the position of $37^{th}$ is substituted with arginine (Arg) from an N-terminal of any one amino acid sequence which is selected from a group comprised of a first immunoglobulin G binding region C1 (PG-C1), a second immunoglobulin G binding region C2 (PG-C2), and a third immunoglobulin G binding region C3 (PG-C3) of a protein G, a protein G variant having photoactivity which introduces pM to the protein G variant, and a method for preparing the same.

Further, still yet another object of the present invention provides polynucleotide encoding the protein G variant and an expression vector comprising the same.

Further, still yet another object of the present invention provides a photomethionine (pM)-introduced protein G variant having photoactivity constituted by an amino acid sequence in which glutamine (Gln) at the position of $32^{nd}$, asparagine (Asn) at the position of $35^{th}$, or aspartic acid (Asp) at the position of $40^{th}$ is substituted with methionine (Met) or asparagine (Asn) at the position of $37^{th}$ is substituted with arginine (Arg) from an N-terminal of any one amino acid sequence which is selected from a group comprised of a first immunoglobulin G binding region C1 (PG-C1), a second immunoglobulin G binding region C2 (PG-C2), and a third immunoglobulin G binding region C3 (PG-C3) of a protein G.

Further, still yet another aspect of the present invention provides a method for preparing a pM-introduced protein G variant comprising:

1) preparing an expression vector including polynucleotide encoding the MRS variant and an expression vector including polynucleotide encoding the protein G variant, respectively;

2) preparing a transformant by simultaneously introducing the expression vectors of the step 1) into *Escherichia coli*; and 3) expressing the pM-labeled protein G variant by culturing the transformant of the step 2).

Further, still yet another aspect of the present invention provides a fusion protein coupled with the protein G variant and an antibody or a fragment of the antibody.

Further, still yet another aspect of the present invention provides a biochip and a biosensor comprising an antibody or a fragment of the antibody coupled with the protein G variant.

Further, still yet another aspect of the present invention provides a nanoparticle delivery system for an antibody-labeled intravenous injection comprising an antibody or a fragment of the antibody coupled with the protein G variant.

Advantageous Effects

A *Escherichia coli* methionyl tRNA synthase (MRS) variant of the present invention is a variant capable of effectively biosynthesizing a photomethionine (pM)-introduced target protein as compared with the wild-type MRS, and thus the pM-labeled protein biosynthesized through the MRS variant of the present invention can be used as an important tool to analyze other polymers which are specifically bound with a specific protein. Further, the pM-introduced protein G variant using the MRS variant has a specific high-efficiency covalent bond with an antibody through high orientation and UV irradiation, and thus the pM-introduced protein G variant can be utilized for developing an antibody chip for blood sample analysis, a highly sensitive biochip, a biosensor, and a cell-capturing chip.

●: Illustrate amino acids expressed after mutation and position;

▲: Illustrate stop codon; and

★: Illustrate introduced cysteine position.

Figure 13:
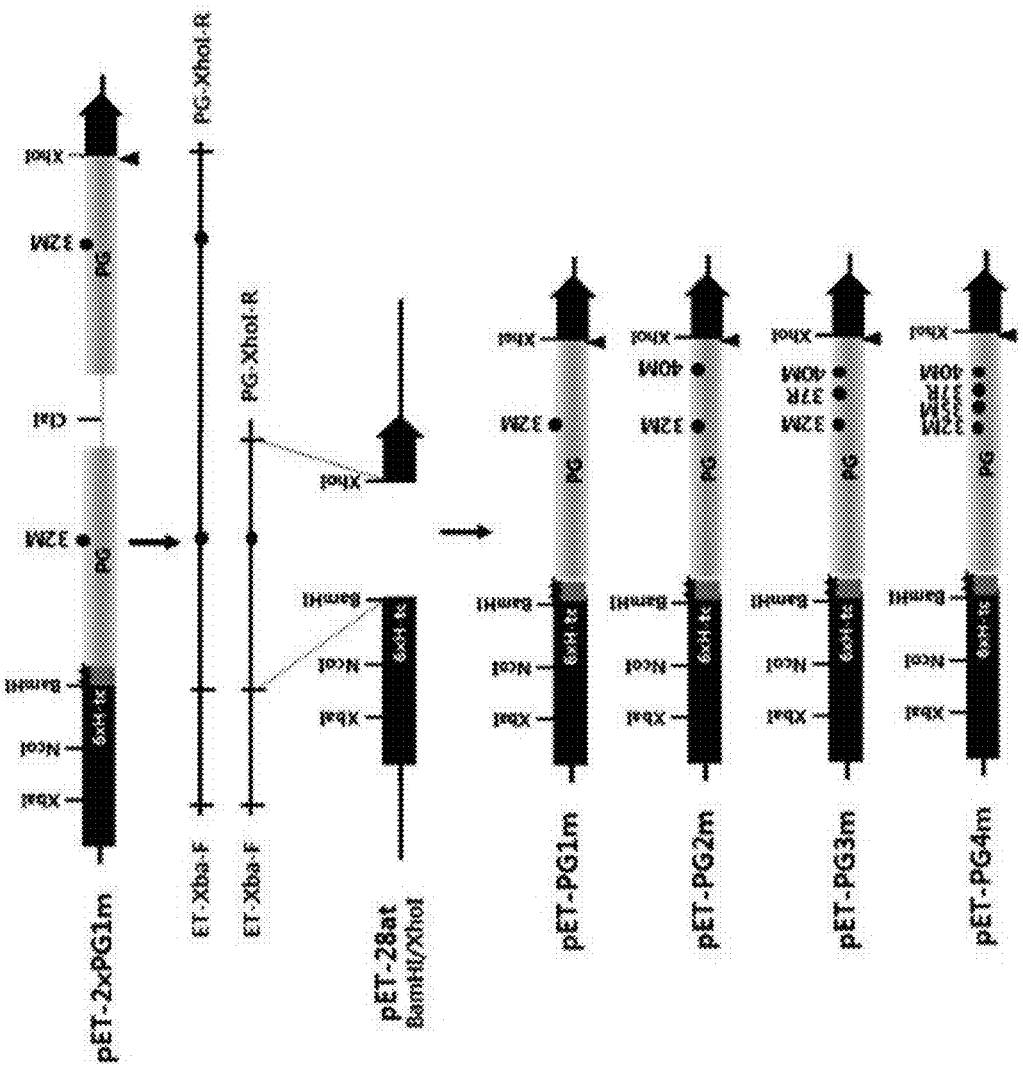

FIG. 13 is a mimetic diagram illustrating a structure of prepared pET-PG variant plasmid.

●: Illustrate amino acids expressed after mutation and position;

▲: Illustrate stop codon; and

★: Illustrate introduced cysteine position.

Figure 14:
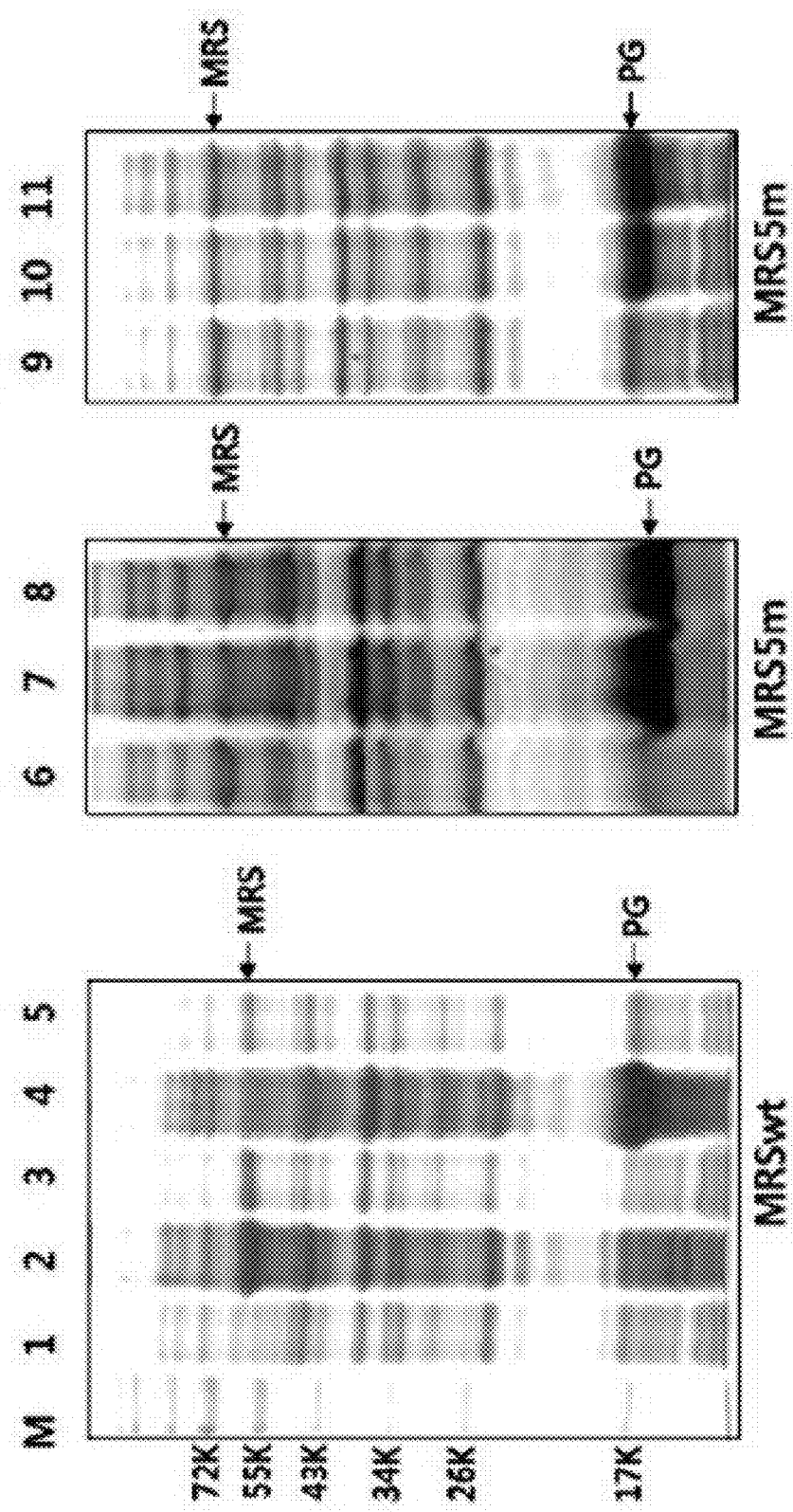

FIG. 14 is a diagram illustrating an expression amount of a pM-labeled protein G by introducing a normal MRS (MRSwt) or MRS5m.

Figure 15:
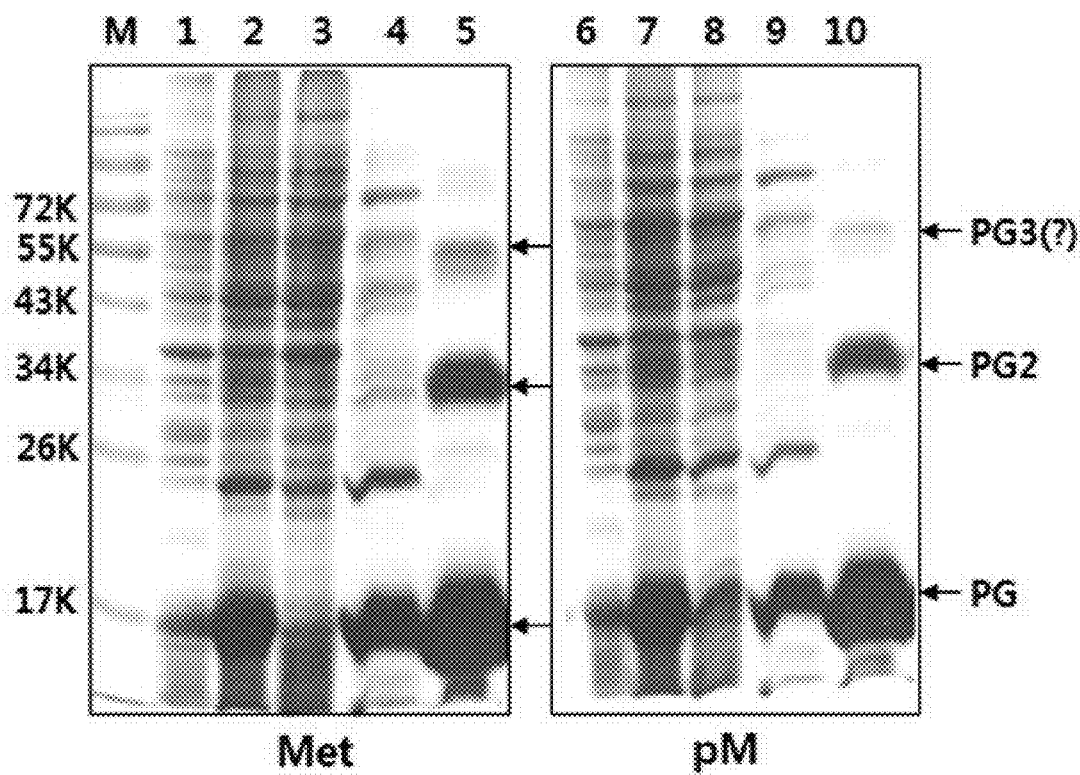

1: Before co-expression of MRSwt and 6H-2×PG2m and induction of LB and arabinose MRSwt;

2: After co-expression of MRSwt and 6H-2×PG2m, co-expression of MRSwt and 6H-2×PG2m, and induction of LB and arabinose MRSwt;

3: Co-expression of MRSwt and 6H-2×PG2m and M9BV+½ CSM-Met starvation;

4: Co-expression of MRSwt and 6H-2×PG2m, and IPTG induction dissolved with M9BV+Met-contained CSM-Met;

5: Co-expression of MRSwt and 6H-2×PG2m, and IPTG induction dissolved with M9BV+pM-contained CSM-Met;

6: Co-expression of MRS5m and 6H-2×PG2m and M9BV+½ CSM-Met starvation;

7: Co-expression of MRS5m and 6H-2×PG2m, and IPTG induction dissolved with M9BV+Met-contained CSM-Met;

8: Co-expression of MRS5m and 6H-2×PG2m, and IPTG induction dissolved with M9BV+pM-contained CSM-Met;

9: Co-expression of MRS5m and 6H-2×PG2m, and IPTG induction dissolved with M9BV+0 mg/ml pM-contained CSM-Met;

10: Co-expression of MRS5m and 6H-2×PG2m, and IPTG induction dissolved with M9BV+0.05 mg/ml pM-contained CSM-Met;

11: Co-expression of MRS5m and 6H-2×PG2m, and IPTG induction dissolved with M9BV+0.1 mg/ml pM-contained CSM-Met;

FIG. 15 is a diagram illustrating a purified shape of 6H-2×PG2m.

1 and 6: Precipitate after sonication;

2 and 7: Supernatant after sonication;

3 and 8: Fraction which is not bound with Ni-NTA agarose;

4 and 9: Release 10 mM imidazole; and 5 and 10: Release 150 mM imidazole.

Figure 16:
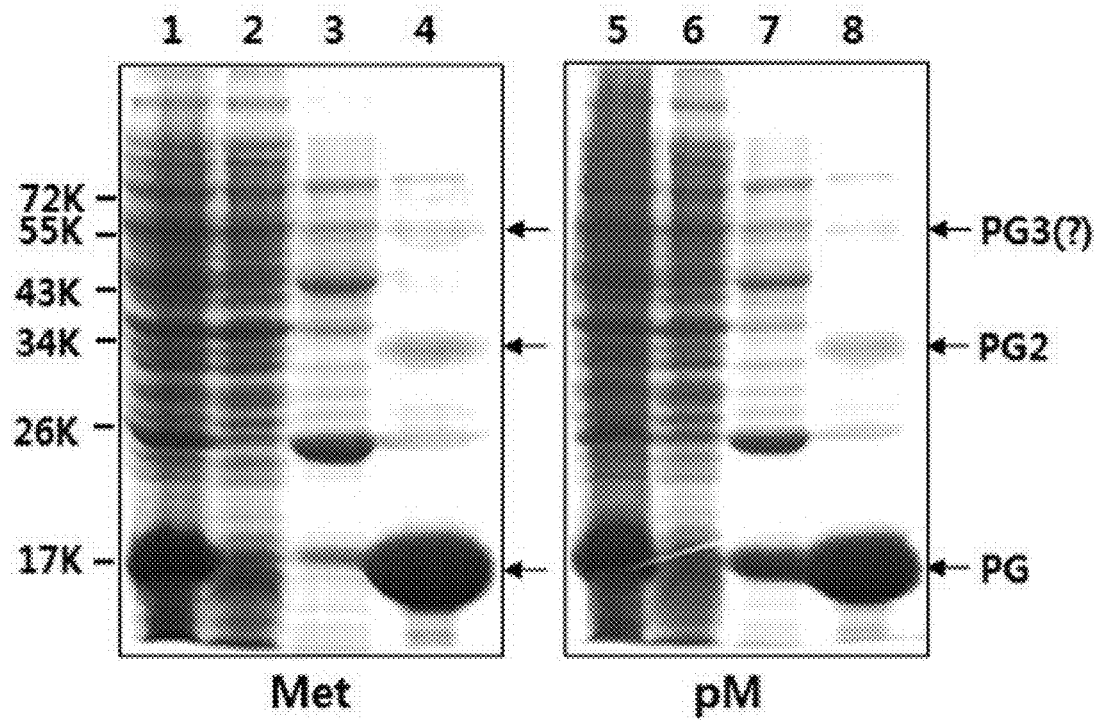

FIG. 16 is a diagram illustrating a purified shape of 6H-2×PG3m.

1 and 5: Supernatant after sonication;

2 and 6: Fraction which is not bound with Ni-NTA agarose;

3 and 7: Release 60 mM imidazole; and 4 and 8: Release 150 mM imidazole.

Figure 17:
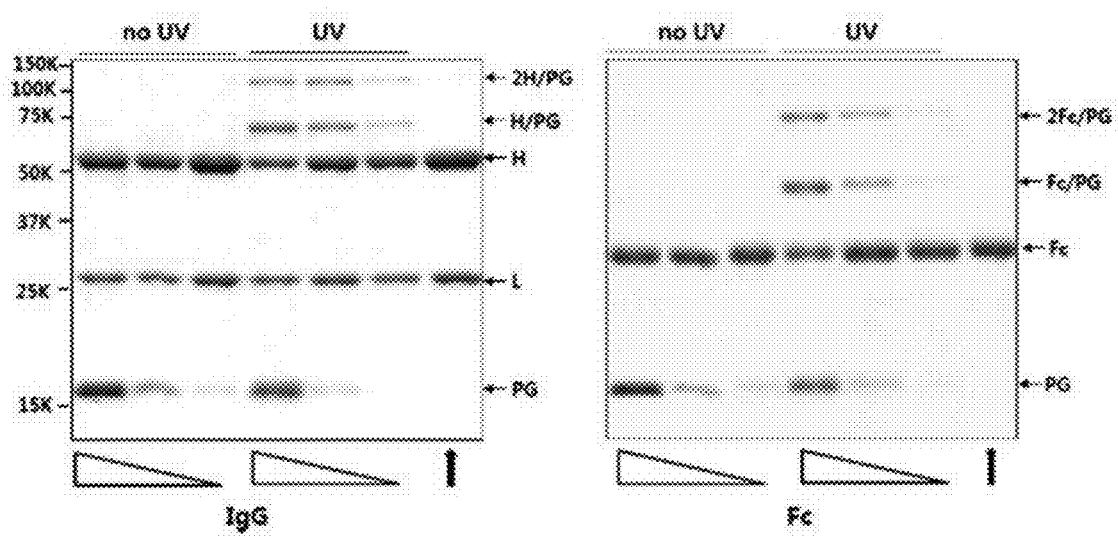

FIG. 17 is a diagram illustrating formation of a photoactivatable covalent bond between a UV-specific pM-labeled 6H-2×PG4m and IgG or Fc.

Figure 18:
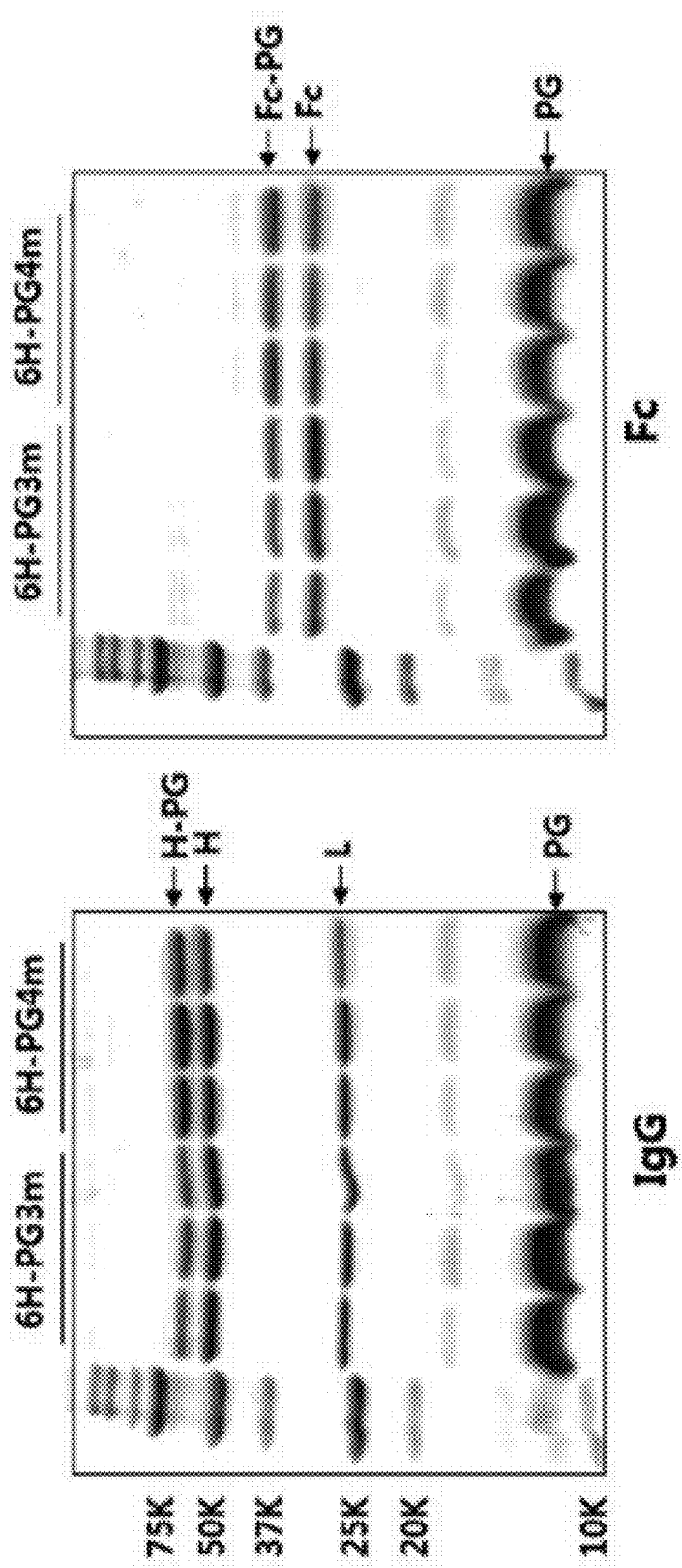

FIG. 18 is a diagram illustrating formation of a photoactivatable covalent bond between a UV-specific pM-labeled 6H-PG4m and IgG or Fc.

Figure 19:
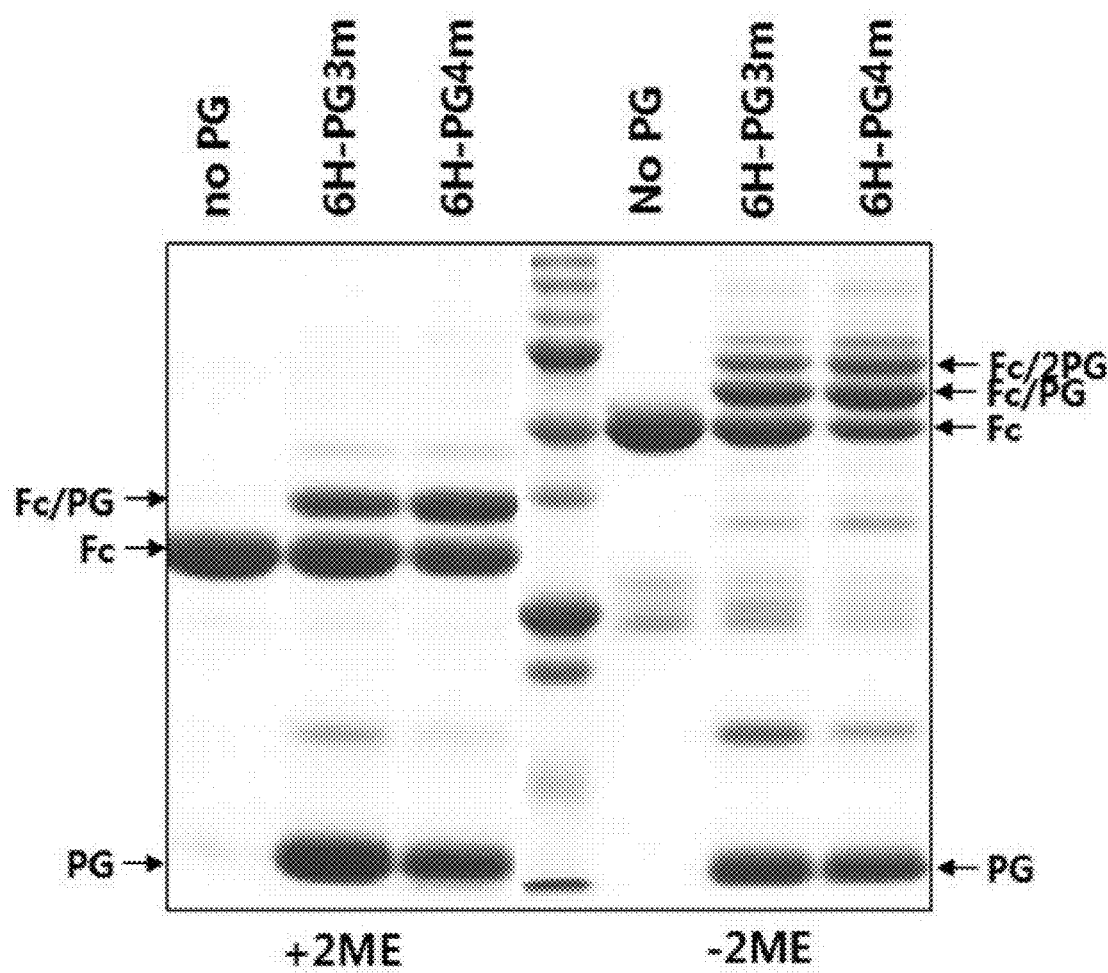

FIG. 19 is a diagram illustrating a shape of a photoactivatable covalent bond between a UV-specific pM-labeled 6H-PG4m or and IgG or Fc according to presence and absence of 2-mercaptoethanol (2ME).

Figure 20:
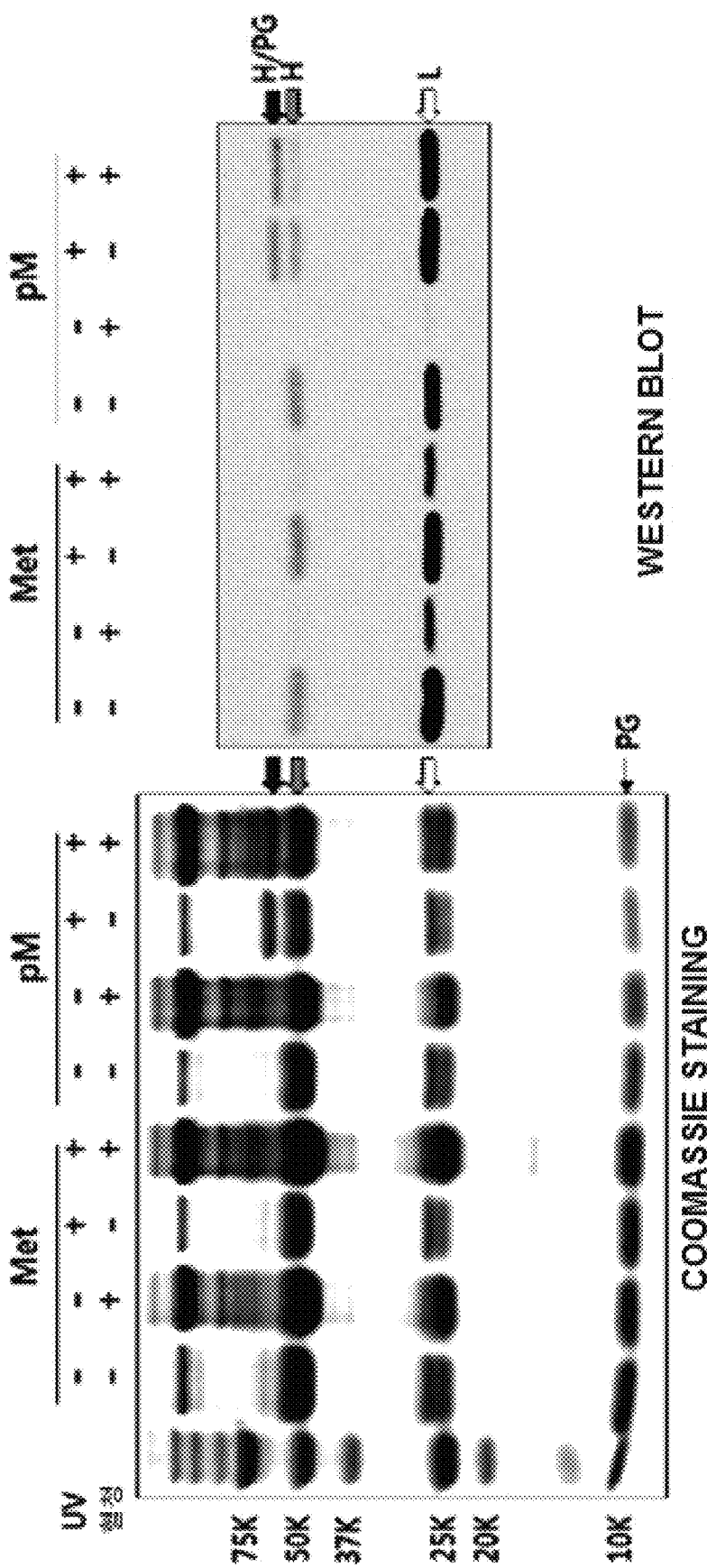

FIG. 20 is a diagram illustrating a substation inhibiting capacity of an antibody in a blood by a covalent bond between IgG and a protein G.

Figure 21:
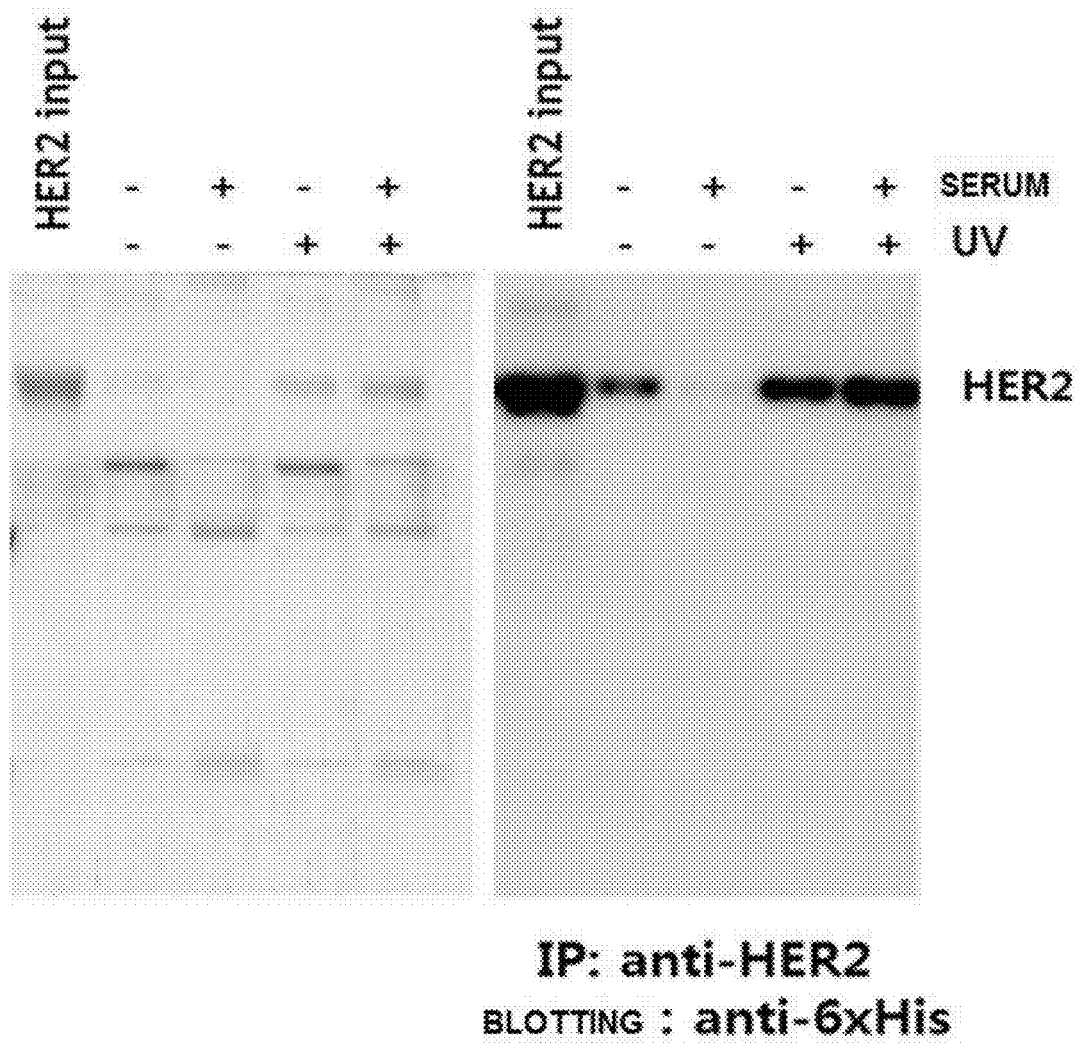

FIG. 21 is a diagram illustrating availability when a conjugate of the IgG and the protein G captures an antigen in the blood.

Figure 22:
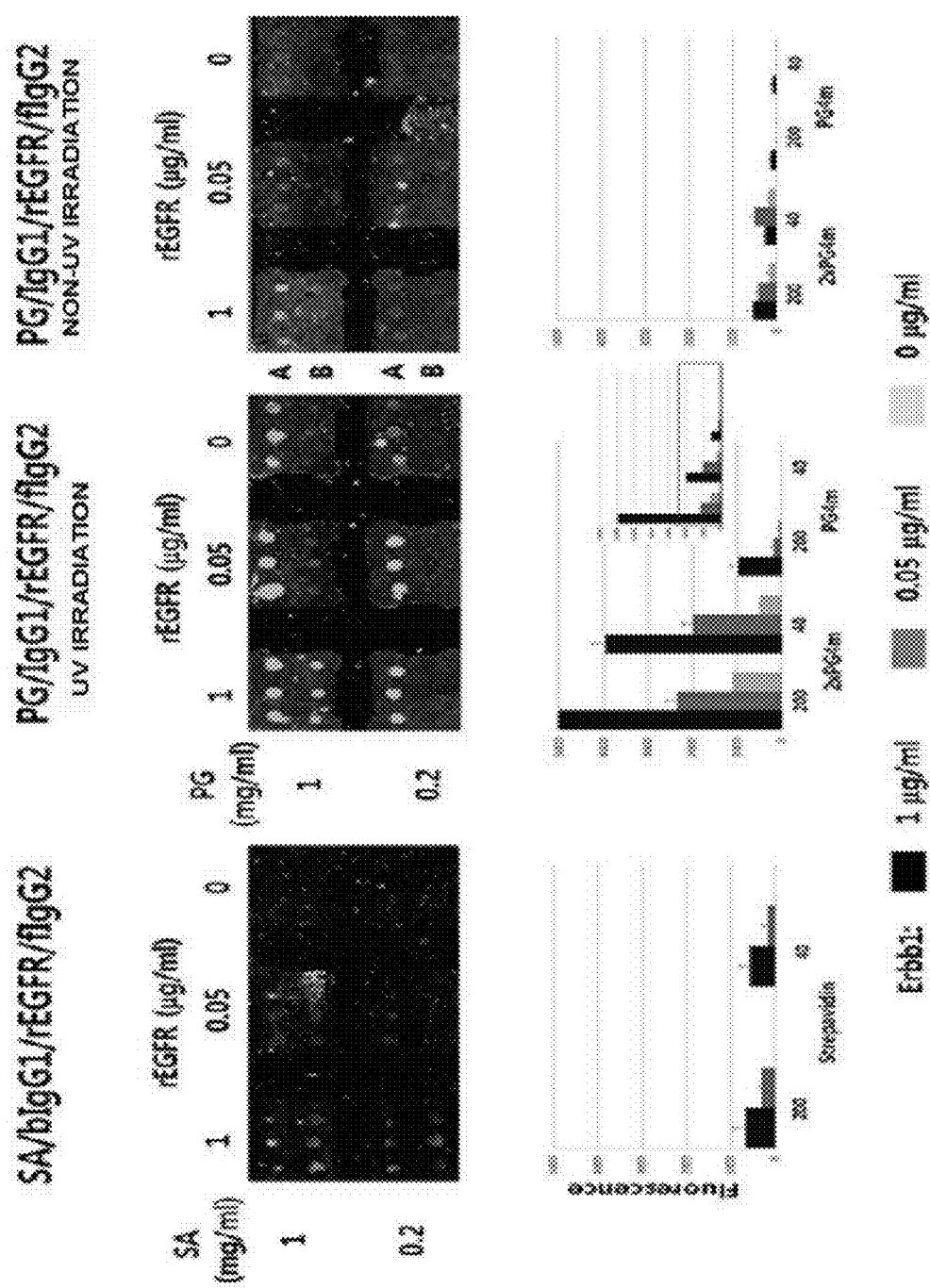

FIG. 22 is a diagram illustrating an effect when a conjugate of the IgG and the protein G detects an antigen in the blood. A streptavidin (SA)/biotinylated IgG (bIgG) system which is frequently used in the related art is used as a control group.

rEGFR: Recombinant epidermal growth factor acceptor ectodomain.

IgG 1: Anti-EGFR human antibody (Erbitux)

fIgG2: FITC-labeled anti-EGFR rat antibody

A: 6H-2×PG4m and

B: 6H-PG4m

Figure 23:
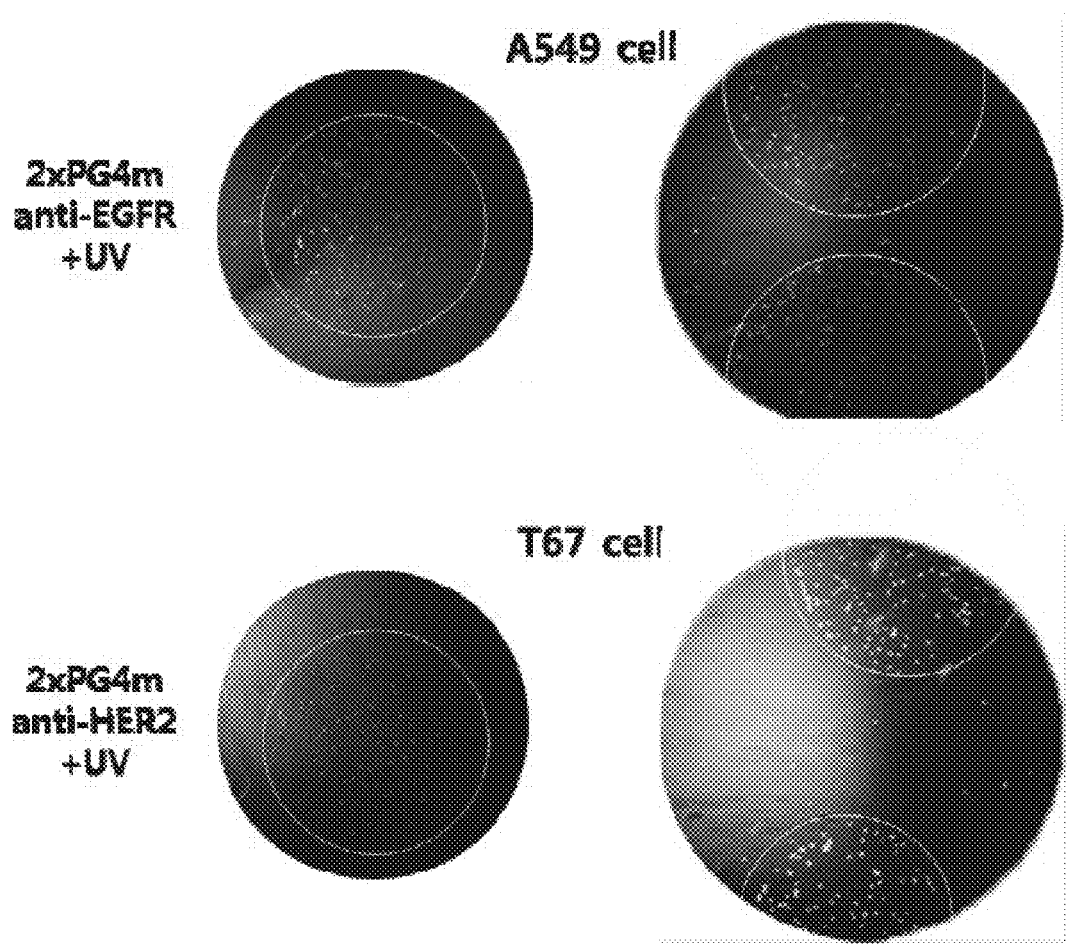

FIG. 23 is a diagram illustrating availability when a conjugate of the IgG and the protein G captures a specific cell in the blood.

Figure 24:
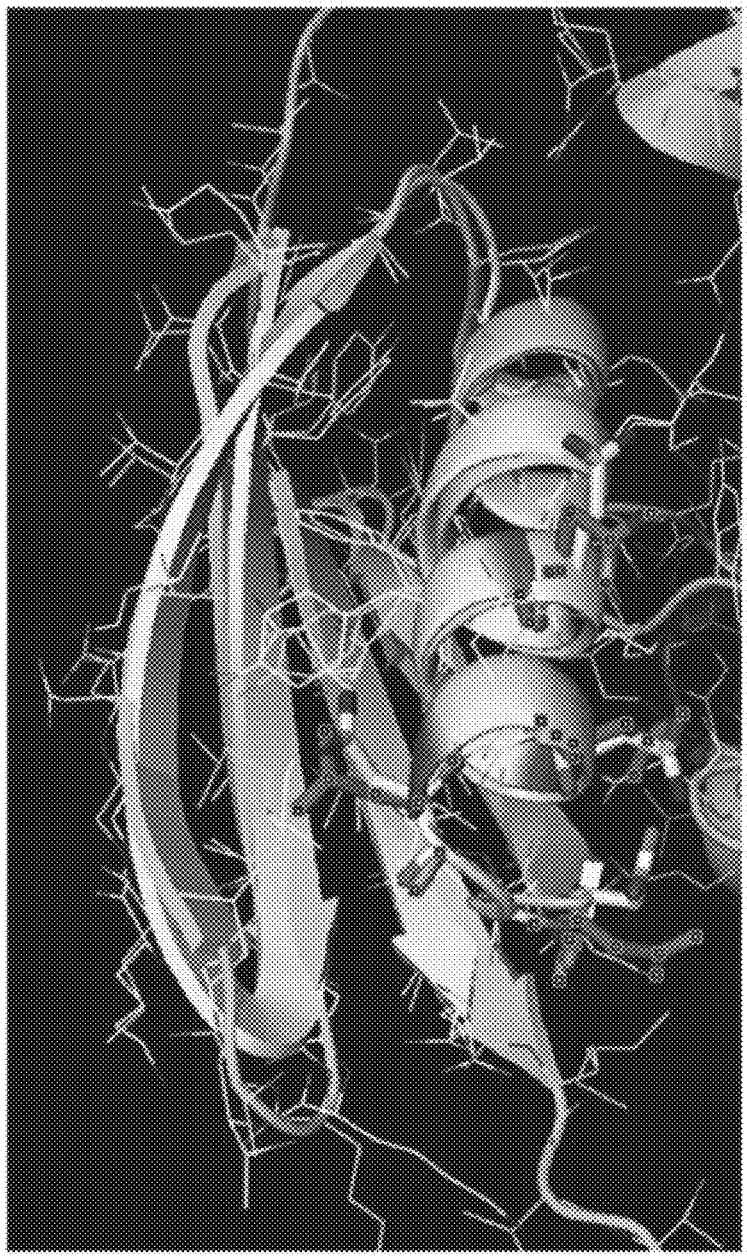

FIG. 24 is a diagram illustrating a tertiary structure of a first immunoglobulin G binding region C1 (PG-C1), a second immunoglobulin G binding region C2 (PG-C2), and a third immunoglobulin G binding region C3 (PG-C3) of a protein G.

Green: Amino acid variant having a slight functional difference as compared with PG-C1; red: Amino acid variant having a relatively large functional difference;

Blue: In the present invention, the amino acid variant is very well preserved in the tertiary structure as substituted amino acids (Q32, N35, N37, and D40); Yellow-pink: PG-C2;

Sky-white: PG-C3, substituted regions are represented by pink and white; and Green: Antibody Fc site.

MODES OF THE INVENTION

Hereinafter, the present invention will be described in detail.

The present invention provides a methionyl tRNA synthase (MRS) variant for introducing photomethionine (pM) to a target protein.

The MRS variant is preferably constituted by an amino acid sequence in which alanine at the position of $12^{th}$ is substituted with glycine, leucine at the position of $13^{th}$ by serine, tyrosine at the position of $260^{th}$ by phenylalanine, isoleucine at the position of $297^{th}$ by valine, and histidine at the position of $301^{st}$ by leucine from an N-terminal of the amino acid sequence of a wild-type *Escherichia coli* MRS, but is not limited thereto.

The wild-type *Escherichia coli* MRS is constituted by an amino acid sequence of SEQ ID NO: 1, but is not limited thereto.

The wild-type *Escherichia coli* MRS is made from a sequence from which a C-terminal is removed, but is not limited thereto.

The target protein may use all proteins as well as an enhanced green fluorescence protein (EGFP) and a factor inhibiting hypoxia inducible factor (FIH) which are used in the exemplary embodiment.

Figure 1:
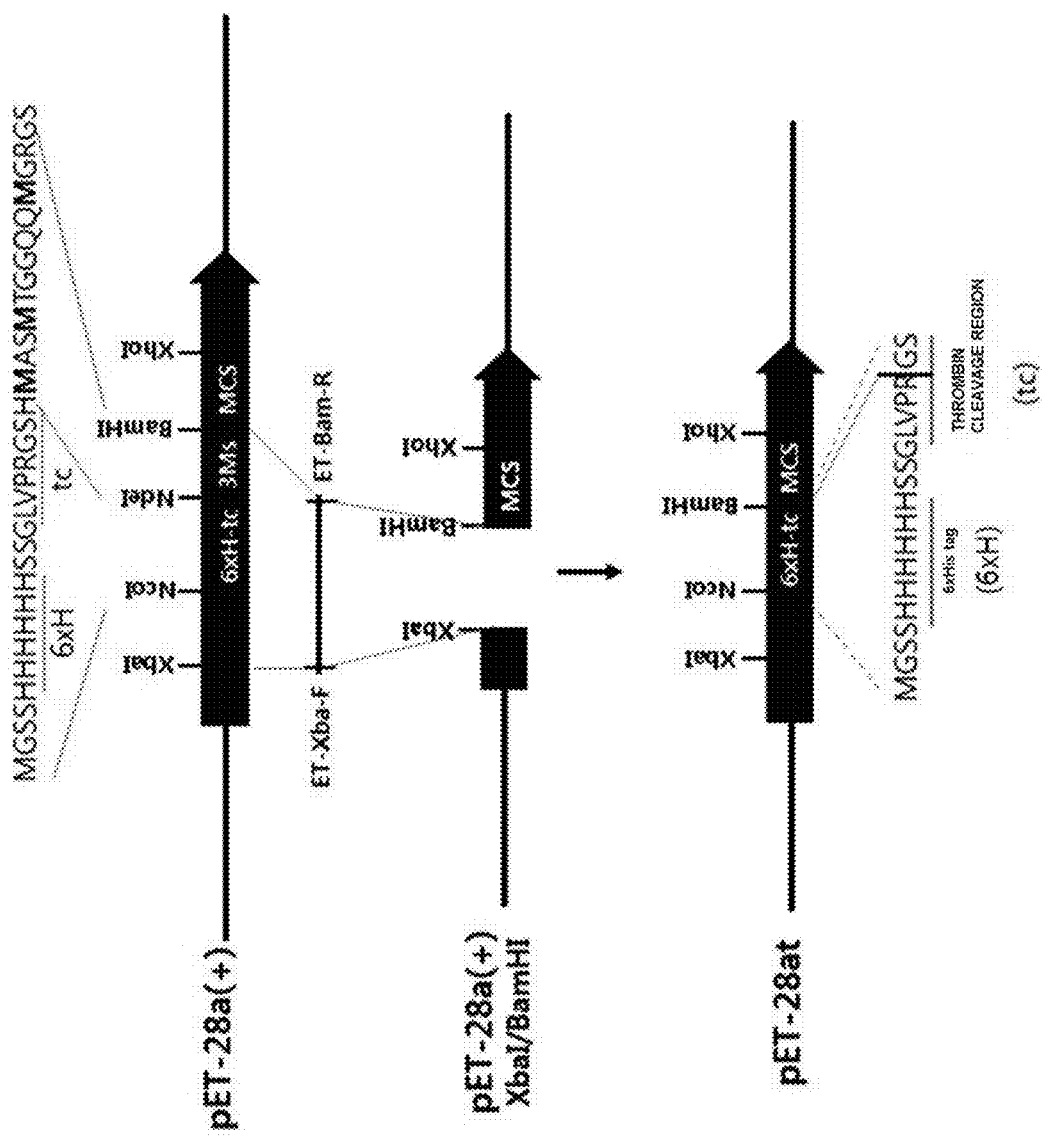
FIG. 1 is a mimetic diagram illustrating preparation of a pET-28at vector for cloning a photomethionine (pM)-labeled protein. 6×H represents a histidine tag and tc represents a thrombin cleavage site.
Figure 2:
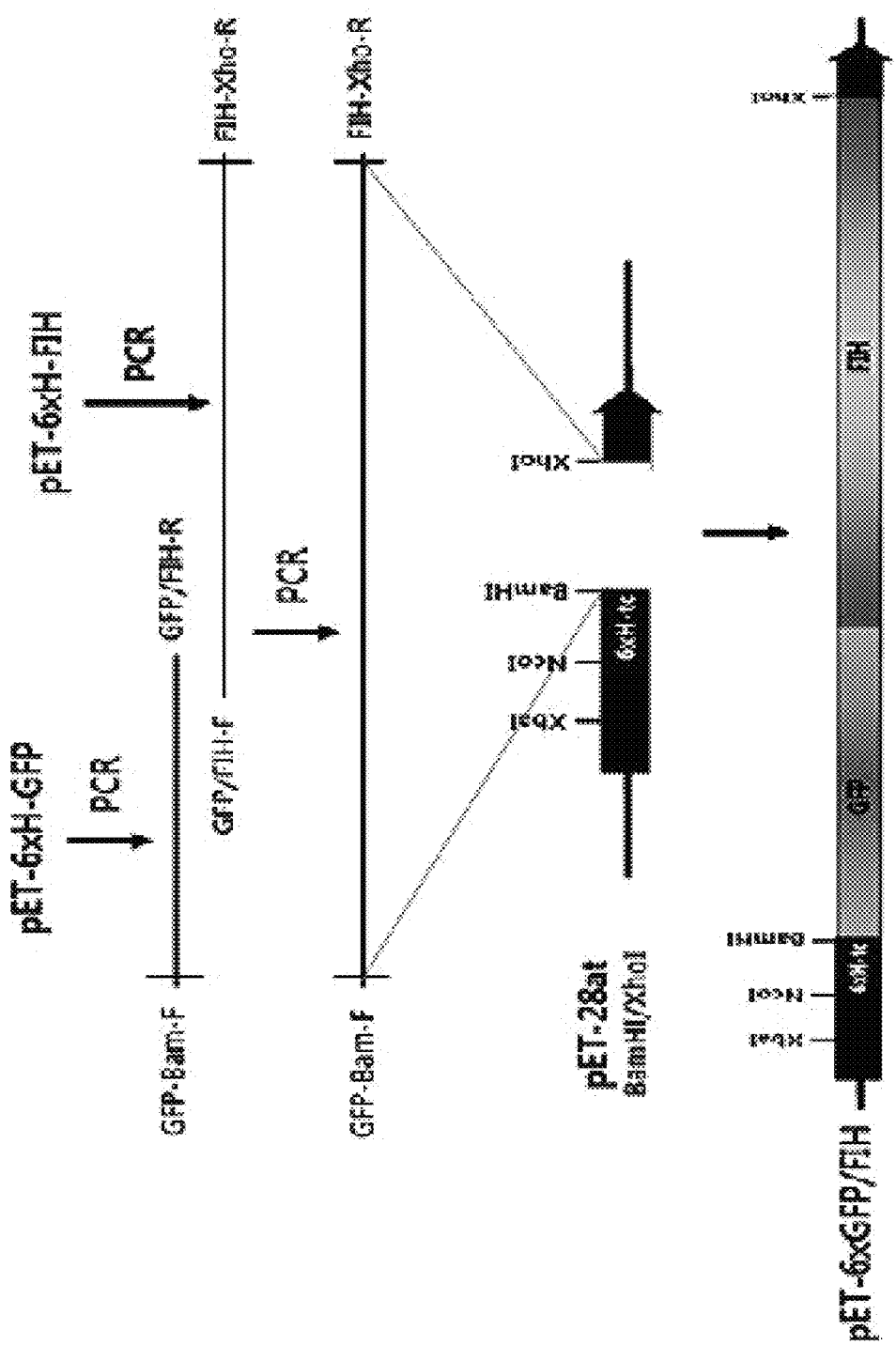
FIG. 2 is a mimetic diagram illustrating preparation of a pET-GFP/FIH plasmid for expressing a GFP/FIH junction protein.

In an exemplary embodiment of the present invention, the inventors prepared a vector for cloning the target protein and perform gene-cloning for expressing the EGFP, the FIH, and an EGFP-FIH as a target protein tagged with 6× histidine (6×H) by using the vector (See FIGS. 1 and 2). Further, the inventors prepared an MRS variant through point mutation by cloning the wild-type MRS gene from which the C-terminal is removed (See FIGS. 3 and 4).

Further, the inventors verified that as a result of expressing a target protein of EGFP, FIH, or GFP-FIH in a medium including methionine or pM as a methionine nutrient by transforming the prepared target protein expression vector in *E. coli* B834, the target protein was expressed in the methionine treatment, but the target protein was not nearly expressed in the pM treatment.

Further, the inventors verified that as a result of expressing a target protein in a medium including methionine or pM as a methionine nutrient by transforming the prepared target protein expression vector and the MRS variant expression vector in *E. coli* B834, the target protein of EGFP, FIH, or GFP-FIH was expressed in the methionine treatment under a condition where the wild-type MRS was expressed, but the target protein was not nearly expressed in the pM treatment (see FIGS. 5 and 7) and verified that MRS1pm and MRS3pm variants causing mutation at previously known positions of $13^{th}$, $260^{th}$, and $301^{st}$ did not show an increase in the protein expression by pM like the wild-type MRS. However, in the case of expressing the MRS5pm variant, it was verified that a 6×H-EGFP protein was expressed even when the pM was treated in the same manner as when the methionine was treated (see FIGS. 5 and 7). As a result, the inventors verified that binding of the wild-type MRS and methionine was easy, but due to a structure of pM having an exposed diazirine group as compared with methionine, like the wild-type MRS, an MRS having Ala12 and Ile297 had an insufficient space in which the pM may approach a ligand binding region, and thus the binding of the pM was difficult, but verified that the MRS5pm variant had an effect that the pM easily approached the ligand binding region of the MRS by substituting Ala12 and Ile297 residues with glycine and valine, respectively, in order to remove a methyl group (see FIG. 8).

Figure 9:
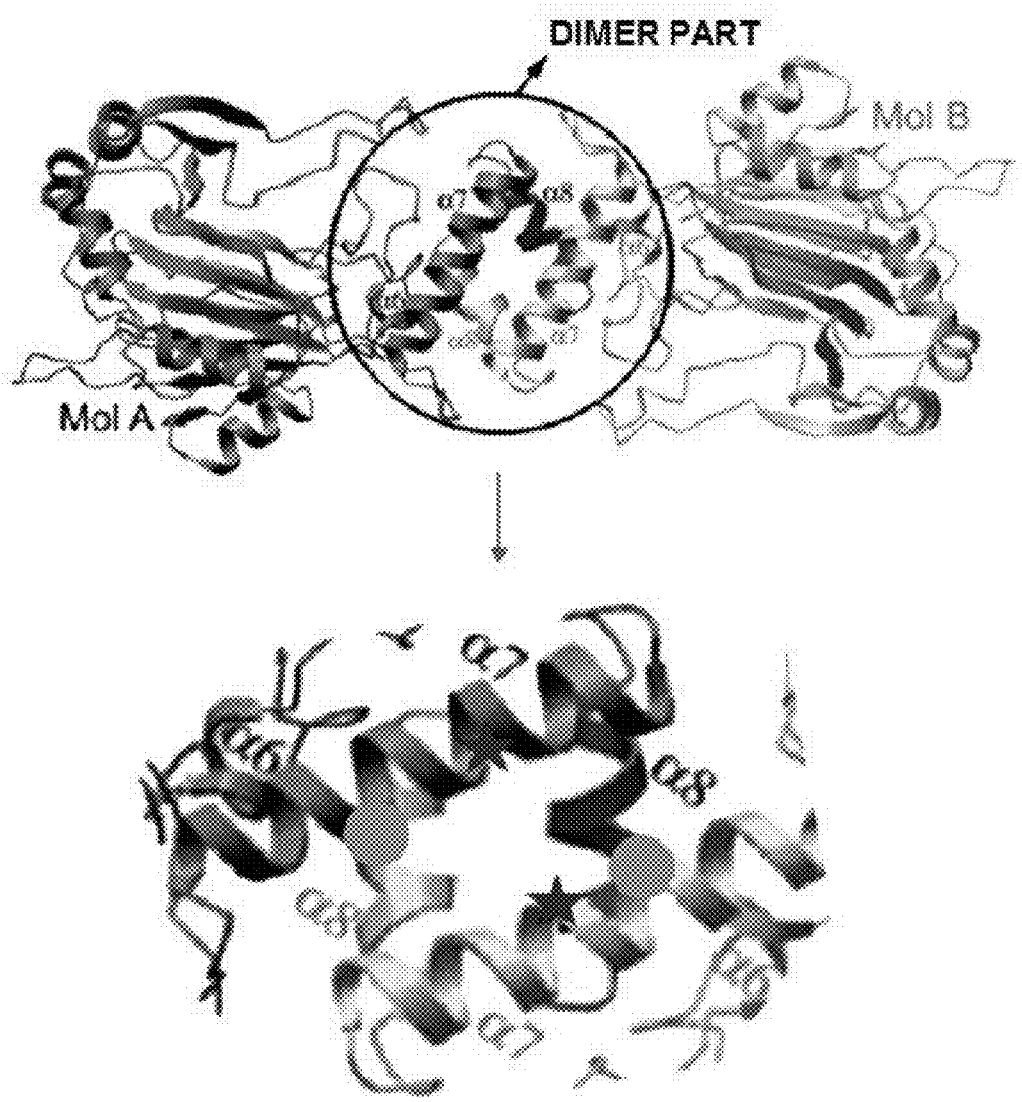
FIG. 9 is a diagram illustrating a structure of an FIH dimer. A black circle represents a part involved in dimer formation in a carboxyl terminal, a green circle and a red star represent three methionine residues which are present in the dimer formation part, and the green circle represents two methionine residues which are very closely present.

Further, the inventors verified that an effect of introducing the pM to the target protein of EGFP, FIH or GFP-FIH was improved by substituting Leu13, Tyr260 and His301 as binding regions of an existing known substrate with serine, phenylalanine and leucine, respectively, in order to optimize the binding of the pM (see FIG. 9).

Figure 10:
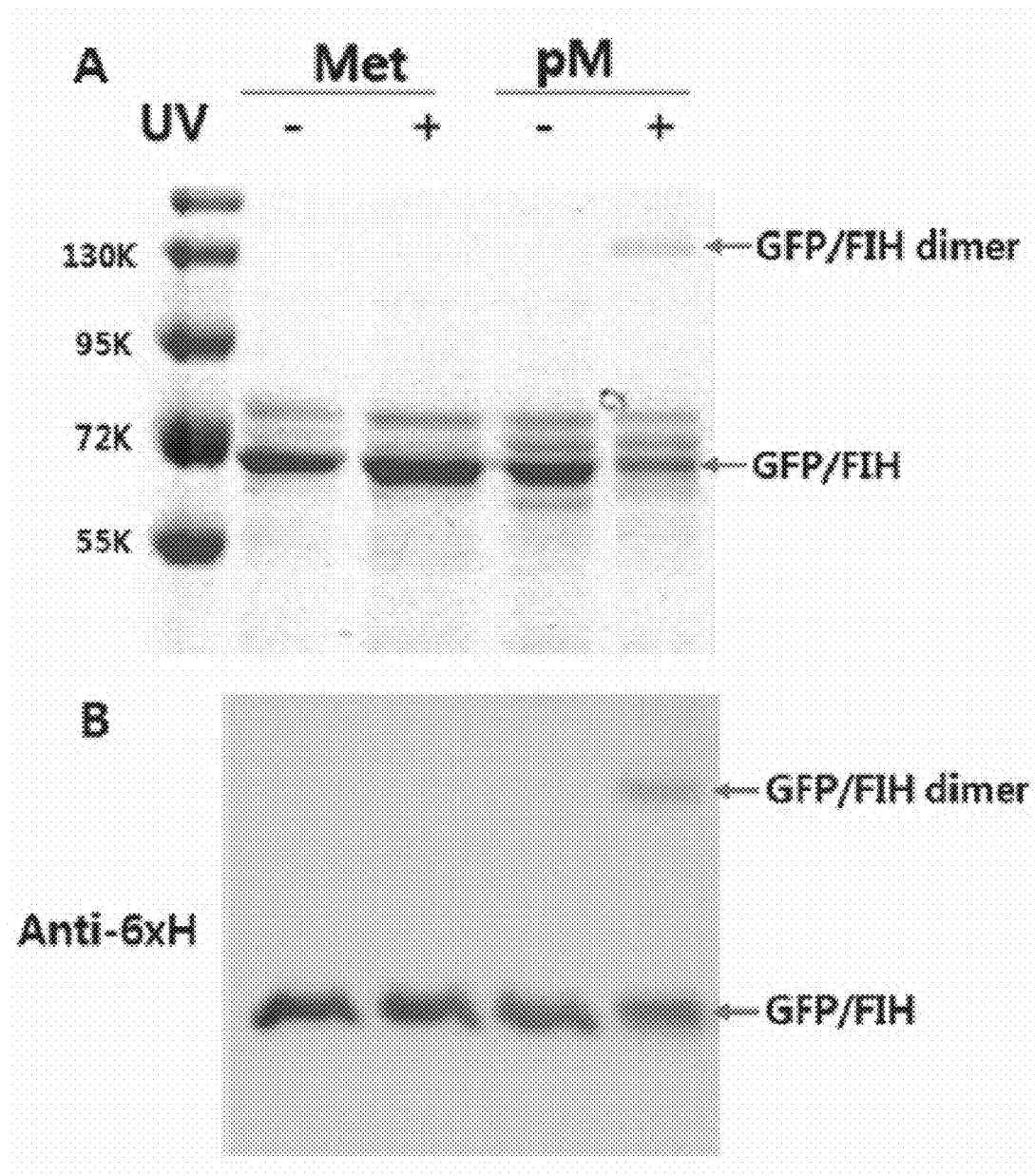
FIG. 10 is a diagram of verifying a dimer of FIH according to whether to irradiate UV having a wavelength of 365 nm. A represents SDS-PAGE stained with coomassie and B represents western blot for an anti-6×H antibody.

Further, the inventors verified that a dimer of the GFP-FIH target protein was formed through photoactivatable covalent bond by partially separating and purifying the 6×H-target protein labeled with the pM through a Ni-NTA-agarose chromatography (see FIG. 8) and irradiating UV having a wavelength of 365 nm through SDS-polyacrylamide gel and western blotting (see FIG. 10).

Accordingly, it was verified that the MRS variant of the present invention may significantly biosynthesize the pM-labeled target protein.

Further, the present invention provides a method for preparing an MRS variant for introducing pM to a target protein made through point mutation of a wild-type *Escherichia coli* MRS.

The MRS variant is preferably constituted by an amino acid sequence in which alanine at the position of $12^{th}$ is substituted with glycine, leucine at the position of $13^{th}$ by serine, tyrosine at the position of $260^{th}$ by phenylalanine, isoleucine at the position of $297^{th}$ by valine, and histidine at the position of 301$^{st}$ by leucine from the N-terminal of the entire amino acid sequence, but is not limited thereto.

The MRS variant of the present invention may be prepared by introducing a mutant into a wild-type *Escherichia coli* MRS gene. A method of introducing a desired mutant into a base sequence of nucleic acid may use any method known in the art such as point mutation, a PCR using oligonucleotide causing degeneracy, a cell mutation inducer including nucleic acid, or radiation exposure.

Further, the present invention provides a reagent composition for introducing pM into a target protein including the MRS variant.

The reagent composition including the MRS variant of the present invention may efficiently biosynthesize the pM-introduced target protein, and thus the pM-labeled target protein may be significantly biosynthesized by using the reagent composition.

Further, the present invention provides a method of introducing pM into a target protein comprising: 1) preparing an expression vector including polynucleotide encoding the target protein and an expression vector including polynucleotide encoding the MRS variant;

2) preparing a transformant by simultaneously introducing the expression vectors of the step 1) into *Escherichia coli*; and 3) expressing the pM-labeled target protein by culturing the transformant of the step 2).

The expression vector is preferably a plasmid vector, a cosmid vector, a bacteriophage vector, and a virus vector and more preferably a plasmid vector, but is not limited thereto.

The culture comprises:

1) transforming simultaneously a plasmid for MRS variant expression and a plasmid for target protein expression in *Escherichia coli*;

2) inducing expression of the MRS variant by adding L-arabinose to the transformant of the step 1);

3) removing methionine from a culture medium of the transformant of the step 1); and 4) expressing the pM-labeled protein in a pM-containing minimal medium, but is not limited thereto.

In the polynucleotide encoding the MRS variant of the present invention, it can be understood by those skilled in the art that due to the degeneracy or in consideration of a codon preferred in an organism to express the antibody, various modifications may be formed in a coding area in a range without changing an amino acid sequence of the antibody expressed from the coding area, various modifications or equations may be formed in a range without influencing the expression of the gene even in a part except for the coding area, and the modified gene is also included in the scope of the present invention. That is, the polynucleotide of the present invention may be mutated by substation, deletion, insertion, or a combination thereof of one or more nucleic acids so long as coding a protein having the equivalent activity and the polynucleotides are included in the scope of the present invention. The sequence of the polynucleotide may have a single chain or a double chain and may be a DNA molecule or an RNA (mRNA) molecule.

When preparing the expression vector, an expression regulation sequence such as a promoter, a terminator, and an enhancer, a sequence for membrane targeting or secretion, and the like are properly selected according to a kind of host cell to produce the MRS variant and variously combined according to an object.

The expression vector of the present invention includes a plasmid vector, a cosmid vector, a bacteriophage vector, a virus vector, and the like, but is not limited thereto. The suitable expression vector includes a signal sequence or a leader sequence for membrane targeting or secretion in addition to expression regulating elements such as a promoter, an operator, a start codon, a termination codon, and an enhancer and may be variously prepared according to an object. The promoter of the expression vector may be constitutive or inducible. Further, the expression vector may include a selection marker for selecting the host cell including the vector and includes a replication origin in the case of a replicable expression vector.

After the expression vector of the present invention is transformed into *E. coli* which is a suitable host cell, the MRS variant according to the present invention may be mass-produced by culturing the transformed host cell. A culture method, a medium condition, and the like which are suitable for the host cell may be easily selected by well-known techniques which are known by those skilled in the art. The method of introducing the expression vector into the host cell may also use any method which is known to those skilled in the art.

Further, the present invention provides a protein G variant constituted by an amino acid sequence in which glutamine (Gln) at the position of 32$^{nd}$, asparagine (Asn) at the position of 35$^{th}$, or aspartic acid (Asp) at the position of 40$^{th}$ is substituted with methionine (Met) or asparagine (Asn) at the position of 37$^{th}$ is substituted with arginine (Arg) from an N-terminal of any one amino acid sequence which is selected from a group comprised of a first immunoglobulin G binding region C1 (PG-C1), a second immunoglobulin G binding region C2 (PG-C2), and a third immunoglobulin G binding region C3 (PG-C3) of a protein G.

The first immunoglobulin G binding region of the protein G is preferably constituted by an amino acid sequence of SEQ ID NO: 2, but is not limited thereto.

The second immunoglobulin G binding region of the protein G is preferably constituted by an amino acid sequence of SEQ ID NO: 3, but is not limited thereto.

The third immunoglobulin G binding region of the protein G is preferably constituted by an amino acid sequence of SEQ ID NO: 4, but is not limited thereto.

One or two of the first immunoglobulin G binding region, the second immunoglobulin G binding region, or the third immunoglobulin G binding region of the protein G may be included, but is not limited thereto.

In the substituted antibody binding region of the protein G, an amino acid sequence and a tertiary structure among the first immunoglobulin G binding region (SEQ ID NO: 2: TYKLILNGKTLKGETTTEAVDAATAEKVFKQY-ANDNGVDGEWTYDDATKT FTVTE), the second immunoglobulin G binding region (SEQ ID NO: 3: TYKLVING-KTLKGETTTEAVDAATAEKVFKQYANDNGVDGEW-TYDDATKT FTVTE), or the third immunoglobulin G binding region (SEQ ID NO: 4: TYKLVINGKTLKGETTTKAV-DAETAEKAFKQYANDNGVDGVWTYDDATKT FTVTE) are preserved with each other (Olsson et al., Eur J Biochem, 168, 319-24, 1987).

Further, the present invention provides polynucleotide encoding the protein G variant.

Further, the present invention provides an expression vector comprising polynucleotide encoding the protein G variant.

Further, the present invention provides a photomethionine (pM)-introduced protein G variant having photoactivity constituted by an amino acid sequence in which glutamine (Gln) at the position of 32$^{nd}$, asparagine (Asn) at the position of 35$^{th}$ or aspartic acid (Asp) at the position of 40$^{th}$ is substituted with methionine (Met) or asparagine (Asn) at the position of 37$^{th}$ is substituted with arginine (Arg) from an N-terminal of any one amino acid sequence which is selected from a group comprised of a first immunoglobulin G binding region C1 (PG-C1), a second immunoglobulin G binding region C2 (PG-C2), and a third immunoglobulin G binding region C3 (PG-C3) of a protein G.

Figure 11:
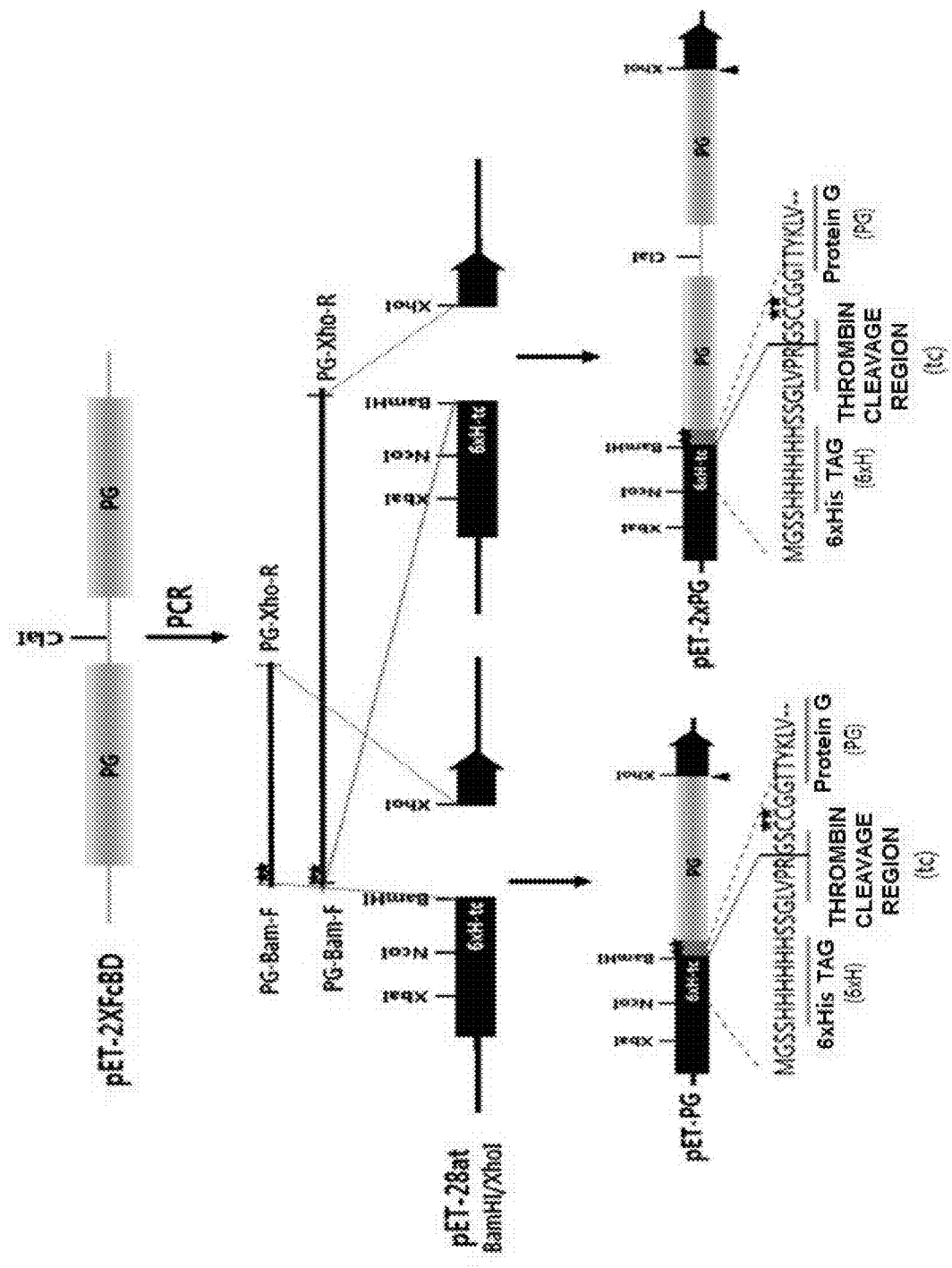
FIG. 11 is a mimetic diagram illustrating a structure of prepared pET-PG and pET-2×PG plasmids.

In the exemplary embodiment of the present invention, the inventors first prepared a vector including one or two protein G motifs in a pET-28at vector (see FIG. 1) tagged with 6× histidine (6×H) prepared in an exemplary embodiment, in order to introduce photomethionine which is a methionine mimetic inducing a covalent bond formation by irradiating UV of 330 to 370 nm to the third immunoglobulin G binding region (PG-C3, SEQ ID NO: 4, Olsson et al., Eur J Biochem, 168, 319-24, 1987) of the protein G without a methionine (Met) residue in the sequence (see FIGS. 1 and 11).

Figure 12:
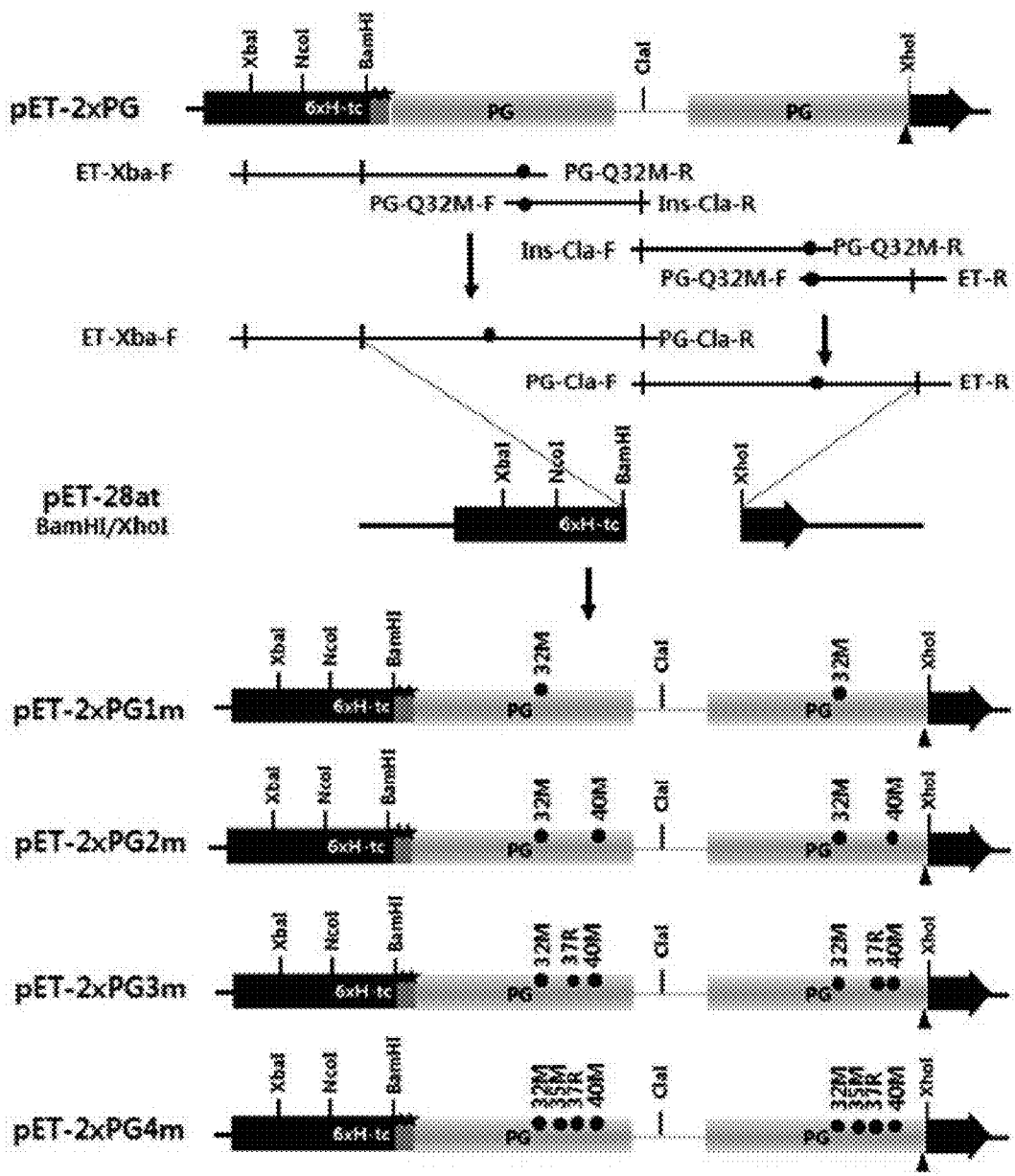
FIG. 12 is a mimetic diagram illustrating a structure of prepared pET-2×PG variant plasmid.

Further, in order to prepare the gene coding the PG-C3 variant introduced with the Met residue, the inventors prepared a pET-2×PG1m in which two PG-C3 motifs are included and glutamine Gln32 at the position of 32$^{nd}$ from an N-terminal of the motif is substituted with Met, a pET-2×PG2m in which two PG-C3 motifs are included and aspartic acid Asp40 at the position of 40$^{th}$ and Gln32 is substituted with Met, a pET-2×PG3m in which two PG-C3 motifs are included and asparagine Asn37 at the position of 37$^{th}$ is substituted with arginine (Arg) and Asp40 and Gln32 are substituted with Met, a pET-2×PG4m plasmid in which two PG-C3 motifs are included and Asn37 is substituted with Arg and asparagine Asn35 at the position of 35$^{th}$, Asp40, and Gln32 are substituted with the Met, a pET-PG1m in which one PG-C3 motif is included and Gln32 from the N-terminal of the motif is substituted with Met, a pET-PG2m in which one PG-C3 motif is included and Gln32 and Asp40 are substituted with Met, a pET-PG3m in which one PG-C3 motif is included and Asn37 is substituted with Arg and Gln32 and Asp40 are substituted with Met, and a pET-PG4m in which one PG-C3 motif is included and Asn37 is substituted with Arg and Gln32, Asp40, and Asn35 are substituted with Met (see FIGS. 12 and 13).

Further, in order to express of the pM-labeled protein G variant, the inventors acquired 6H-2×PG1m, 6H-2×PG2m, 6H-2×PG3m1, 6H-2×PG3m2 and 6H-2×PG4m, 6H-PG1m, 6H-PG2m, 6H-PG3m1, 6H-PG3m2 and 6H-PG4m which are tagged with 6×H by simultaneously transforming a plasmid coding a methionyl tRNA synthase variant (MRS5m) gene prepared in the exemplary embodiment and a plasmid coding the PG-C3 Met variant gene in a Met auxotroph E. coli (E. coli B834) and then expressing the protein G in a minimal medium including pM. It was verified that the expression of the pM-labeled 6H-PG variant is increased by MRS5m (see FIG. 14).

Further, the inventors verified that since the expressed protein G variants had the bound 6×H groups, whether to express the protein G variants was verified by a Ni-NTA agarose chromatography after partially purifying, and as a result, during step gradient, most of 6H-2×PG2m was released from imidazole of 150 Mm, and accordingly, other variants were partially purified under the same condition. It was verified that the expression shape of the partially purified variants formed a monomer and oligomers such as a dimer, a trimer, and a tetramer as a result verified by SDS-PAGE (see FIGS. 15 and 16). Further, as a result of LC/MS/MS mass spectrometry by extracting the dimers, it was verified that a band at the dimer was a derivative including a PG-C3 sequence and a pM labeling rate was 50% or more.

Further, the inventors verified that in order to verify covalent bond between the purified pM-labeled protein G variant and a human antibody IgG, as a result of performing SDS-PAGE analysis and covalent bond formation analysis, when irradiating the UV, covalent bond among the pM-labeled protein G, an IgG heavy chain, and an Fc region was efficiently induced and in this case, as the number of residues substituted with Met was increased, the covalent bond formation rate was increased together (see FIGS. 17 to 19).

Further, the inventors verified that in order to verify a substitution inhibiting capability of an antibody in a blood by covalent bond of the purified pM-labeled protein G variant, a serum was treated in 6H-PG4m covalent-bound with a biotinylated IgG (bIgG) heavy chain (bH) by irradiating UV and then subject to SDS-PAGE, Coomassie staining, and western blotting, and as a result, the conjugate was not nearly influenced by serum treatment (see FIG. 20).

Further, the inventors verified that in order to verify a detection capability of a protein in the blood of the purified pM-labeled protein G variant, the pM-labeled 6H-PG4m and the human antibody was mixed, a covalent bond was induced by treating UV, and then immunoprecipitation was performed, and as a result, in the group irradiating the UV, 6H-HER2 had higher recovery rate after immunoprecipitation up to about 40% and thus, the detection capability of the protein in the blood of the purified pM-labeled protein G variant was excellent (see FIG. 21).

Further, the inventors verified that the antibody analysis capability in the blood of the purified pM-labeled protein G variant and availability when analyzing cells in the blood were verified, and as a result, in the pM-labeled 6H-2× PG4m/antibody system irradiating the UV, it was verified that sensitivity and antibody-specific cell capturing capability were excellent and thus, the pM-labeled protein G variant may be used in a biochip, a biosensor, and cell-capturing (see FIG. 22).

Accordingly, the pM-introduced protein G variant of the present invention forms a high-efficiency covalent bond with an antibody-specific by UV irradiation as well as high orientation, and thus, the pM-introduced protein G variant may be utilized for developing an antibody chip for analyzing a blood sample, a highly sensitive biochip, and a biosensor.

Further, the present invention provides a method of preparing a protein G variant having photoactivity including substituting glutamine (Gln) at the position of 32$^{nd}$, asparagine (Asn) at the position of 35$^{th}$, or aspartic acid (Asp) at the position of 40$^{th}$ with methionine (Met) or substituting asparagine (Asn) at the position of 37$^{th}$ with arginine (Arg) from an N-terminal in any one amino acid sequence which is selected from a group comprised of a first immunoglobulin G binding region C1 (PG-C1), a second immunoglobulin G binding region C2 (PG-C2), and a third immunoglobulin G binding region C3 (PG-C3) of a protein G.

The pM-introduced protein G variant of the present invention forms a high-efficiency covalent bond with an antibody-specific by UV irradiation as well as high orientation, and thus, the method of preparing the protein G variant may be utilized for developing an antibody chip for analyzing a blood sample, a highly sensitive biochip, and a biosensor.

Further, the present invention provides a method for preparing a pM-introduced protein G variant comprising:

1) preparing an expression vector including polynucleotide encoding the MRS variant and an expression vector including polynucleotide encoding the protein G variant constituted by an amino acid sequence in which glutamine (Gln) at the position of 32$^{nd}$, asparagine (Asn) at the position of 35$^{th}$, or aspartic acid (Asp) at the position of 40$^{th}$ is substituted with methionine (Met) or asparagine (Asn) at the position of 37$^{th}$ is substituted with arginine (Arg) from an N-terminal of any one amino acid sequence which is selected from a group comprised of a first immunoglobulin G binding region C1 (PG-C1), a second immunoglobulin G binding region C2 (PG-C2), and a third immunoglobulin G binding region C3 (PG-C3) of a protein G;

2) preparing a transformant by simultaneously introducing the expression vectors of the step 1) into *Escherichia coli*; and 3) expressing the pM-labeled protein G variant by culturing the transformant of the step 2).

The vector of the step 1) is preferably a plasmid vector, a cosmid vector, a bacteriophage vector, and a virus vector and more preferably a plasmid vector, but is not limited thereto.

In the polynucleotide encoding the protein G variant of the present invention, it can be understood to those skilled in the art that due to the degeneracy or in consideration of a codon preferred in an organism to express the antibody, various modifications may be formed in a coding area in a range without changing an amino acid sequence of the antibody expressed from the coding area, various modifications or equations may be formed in a range without influencing the expression of the gene even in a part except for the coding area, and the modified gene is also included in the scope of the present invention. That is, the polynucleotide of the present invention may be mutated by substation, deletion, insertion, or a combination thereof of one or more nucleic acids so long as coding a protein having the equivalent activity and the polynucleotides are included in the scope of the present invention. The sequence of the polynucleotide may have a single chain or a double chain and may be a DNA molecule or an RNA (mRNA) molecule.

When preparing the expression vector, an expression regulation sequence such as a promoter, a terminator, and an enhancer, a sequence for membrane targeting or secretion, and the like are properly selected according to a kind of host cell to produce the MRS variant and variously combined according to an object.

Further, the present invention provides a protein G variant constituted by an amino acid sequence in which glutamine (Gln) at the position of 32$^{nd}$, asparagine (Asn) at the position of 35$^{th}$, or aspartic acid (Asp) at the position of 40$^{th}$ is substituted by methionine (Met) or asparagine (Asn) at the position of 37$^{th}$ is substituted by arginine (Arg) from an N-terminal of any one amino acid sequence which is selected from a group comprised of a first immunoglobulin G binding region C1 (PG-C1), a second immunoglobulin G binding region C2 (PG-C2), and a third immunoglobulin G binding region C3 (PG-C3) of a protein G, or a fusion protein in which an antibody is bound with a pM-introduced protein G variant having photoactivity.

The fragment is preferably an Fc region of the antibody, but is not limited thereto.

The pM-introduced protein G variant of the present invention forms a high-efficiency covalent bond with an antibody-specific by UV irradiation as well as high orientation, and thus, the fusion protein in which the antibody is bound with the protein G variant may be utilized for developing a highly sensitive biochip, a biosensor, and a cell-capturing chip.

Further, the present invention provides a protein G variant constituted by an amino acid sequence in which glutamine (Gln) at the position of 32$^{nd}$, asparagine (Asn) at the position of 35$^{th}$, or aspartic acid (Asp) at the position of 40$^{th}$ is substituted by methionine (Met) or asparagine (Asn) at the position of 37$^{th}$ is substituted by arginine (Arg) from an N-terminal of any one amino acid sequence which is selected from a group comprised of a first immunoglobulin G binding region C1 (PG-C1), a second immunoglobulin G binding region C2 (PG-C2), and a third immunoglobulin G binding region C3 (PG-C3) of a protein G, or a biochip in which a highly oriented antibody is bound with a pM-introduced protein G variant having photoactivity.

Further, the present invention provides a biosensor in which a highly oriented antibody is bound with the protein G variant.

Further, the present invention provides a cell-capturing system in which a highly oriented antibody is bound with the protein G variant.

The pM-introduced protein G variant of the present invention forms a high-efficiency covalent bond with an antibody-specific by UV irradiation as well as high orientation, and thus, the pM-introduced protein G variant may be utilized for developing a highly sensitive biochip, a biosensor, and a cell-capturing chip.

Further, the present invention provides a nanoparticle delivery system for an antibody-labeled intravenous injection including an antibody or a fragment thereof which is bound with a protein G variant constituted by an amino acid sequence in which glutamine (Gln) at the position of 32$^{nd}$, asparagine (Asn) at the position of 35$^{th}$ or aspartic acid (Asp) at the position of 40$^{th}$ is substituted by methionine (Met) or asparagine (Asn) at the position of 37$^{th}$ is substituted by arginine (Arg) from an N-terminal of any one amino acid sequence which is selected from a group comprised of a first immunoglobulin G binding region C1 (PG-C1), a second immunoglobulin G binding region C2 (PG-C2), and a third immunoglobulin G binding region C3 (PG-C3).

The pM-introduced protein G variant of the present invention forms a high-efficiency covalent bond with an antibody-specific by UV irradiation as well as high orientation, and thus, the pM-introduced protein G variant may be utilized for preparing a nanoparticle carrier for a target-oriented injection by immobilizing the antibody to the nanoparticle.

Hereinafter, Examples of the present invention will be described in detail.

However, the following Examples just exemplify the present invention, and the contents of the present invention are not limited to the following Examples.

[Example 1] Preparation of Vector for Cloning Target Protein

In order to prepare a vector for cloning a target protein, three methionine residues were removed between NdeI and BamHI of a pET-28a(+) vector (Novagen, USA).

In detail, pET-28a(+) was used as a template and amplified through PCR by using a forward primer TET-Xba-F (SEQ ID NO: 6: 5'-TTCCCCTCTAGAAATAATTTTGTT-TAAC-3') and a reverse primer ET-Bam-R (SEQ ID NO: 7: 5'-GCGCGGATCCGCGCGGCACCAGGCCGC-3') which introduce a 6× histidine tag 6×H into the N-terminal, and the amplified DNA was cut with XbaI and BamHI to be inserted into a XbaI/BamHI position of the pET-28a(+), and it was called pET-28at.

As a result, as illustrated in FIG. 1, the prepared pET-28at vector was prepared as a vector in which three methionine residues between NdeI-BamHI were removed, but a thrombin cleavage site was maintained, and thus a 6×H site was cleaved and used as a vector for cloning an enhanced green fluorescence protein (EGFP) and a EGFP-factor inhibiting hypoxia inducible factor (FIH), and a protein G (see FIG. 1).

[Example 2] Cloning of Target Protein Expression Gene in pET-28at

In order to express the target protein, a protein expression gene was cloned in the pET-28at vector prepared in Example 1.

In detail, in order to obtain a EGFP protein gene, pEGFP-N3 (BD Biosciences Clontech, USA) was used as a template, amplified through PCR by using a forward primer GFP-Bam-F (SEQ ID NO: 8: 5'-CGGGATCCATGGTGAG-CAAGGGCGAG-3') and a reverse primer GFP-Xho-R (SEQ ID NO: 9: 5'-CCGCTCGAGTTACTTGTACA-GCTCGTC-3'), and inserted into a BamHI/XhoI position of the pET-28at vector, and it was called pET-GFP.

In order to obtain the gene of the GFP-FIH conjugated protein, pEGFP-N3 (BD Biosciences Clontech, USA) was used as a template, and EGFP gene for connecting FIH was amplified by using a GFP-Bam-F forward primer and a GFP/FIH-R reverse primer (SEQ ID NO: 10: 5'-CGCCGCT-GTCCCGCCGAGAGTGATCCCG-3'). In addition, pET-FIH (Lee, et al., Biol Chem, 278, 7558-63, 2003) was used as a template, and FIH gene for connecting EGFP was amplified by using a GFP/FIH-F forward primer (SEQ ID NO: 11: 5'-ACTCTCGGCGGGACAGCGGCGGAG-GCTG-3') and a FIH-Xho-R reverse primer (SEQ ID NO: 12: 5'-TTCCCTCGAGACCCCTGGCAGGCTAG-3'). A GFP-FIH conjugate gene was amplified through PCR by using GFP-Bam-F and FIH-Xho-R primers by mixing two kinds of amplified DNAs and inserted into BamHI and XhoI positions of the pET-28at vector, and it was called pET-GFP/FIH (see FIG. 2).

[Example 3] Cloning of MRS with Cleaved Carboxyl Terminal

In order to prepare a methionyl tRNA synthase (MRS) for synthesizing photomethionine (pM, L-2-amino-5,5-azi-hexanoic acid)-labeled protein, a wild-type MRS gene was cloned to prepare the variant thereof.

Figure 3:
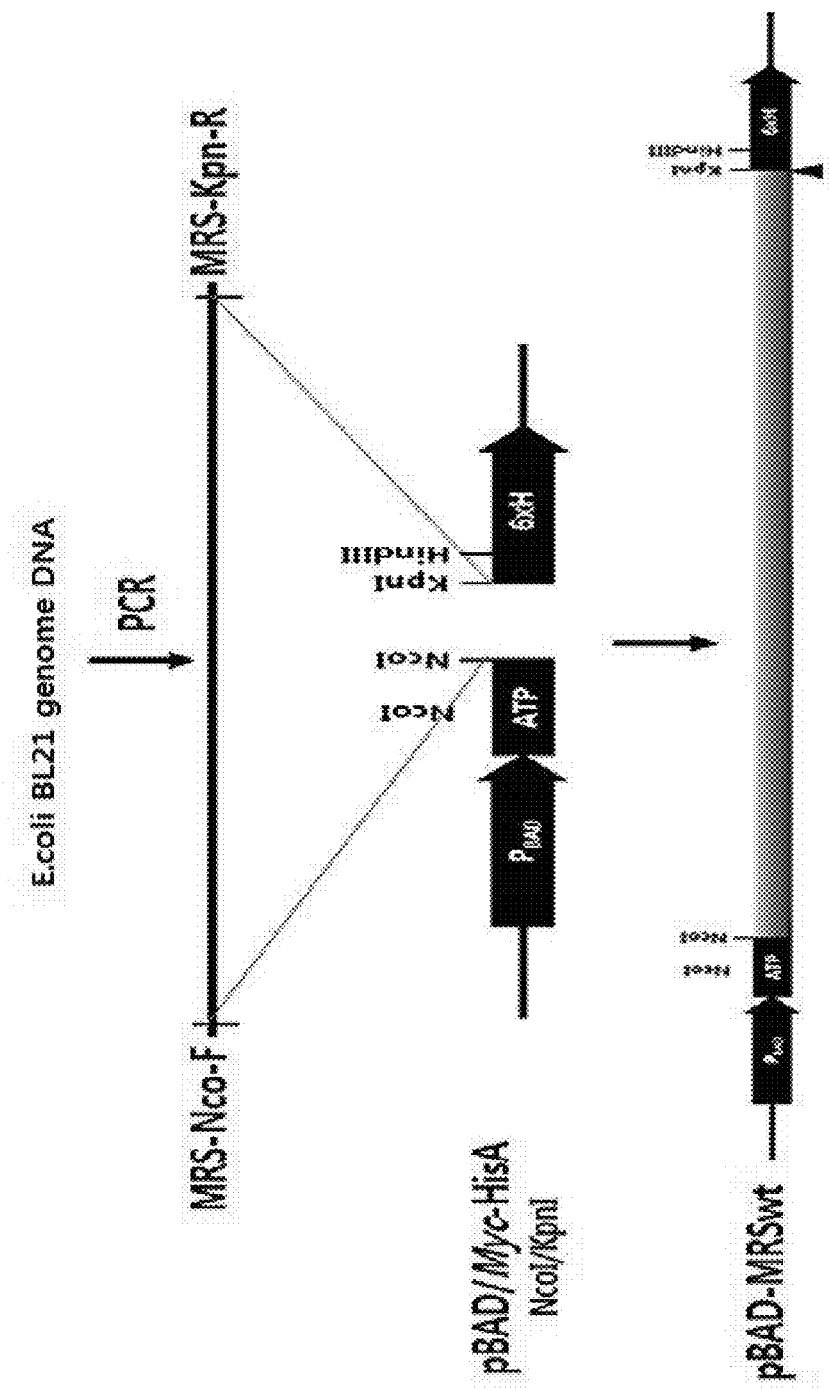
FIG. 3 is a mimetic diagram of preparing a pBAD-MRSwt plasmid in which methionyl tRNA synthase (MRS) (MRS1-548) of which a carboxyl terminal is partially cleaved is cloned in a pBAD/Myc-HisA vector.

In detail, an *E. coli* (*E. coli* BL21) genome DNA extract was used as a template, and a *E. coli* MRS gene consisting of a base sequence of SEQ ID NO: 5 was amplified through PCR by using a MRS-Nco-F forward primer (SEQ ID NO: 13: 5'-ATTCCATGGCTCAAGTCGCGAA-3') and a MRS-Kpn-R reverse primer (SEQ ID NO: 14: 5'-CAGCGGTAC-CTTATTCTTTAGAGGCTTCCACC-3') and inserted into a NcoI/KpnI position of a pBAD/Myc-HisA vector (Invitrogen corporation, USA), and it was called pBAD-MRSwt (see FIG. 3).

Figure 4:
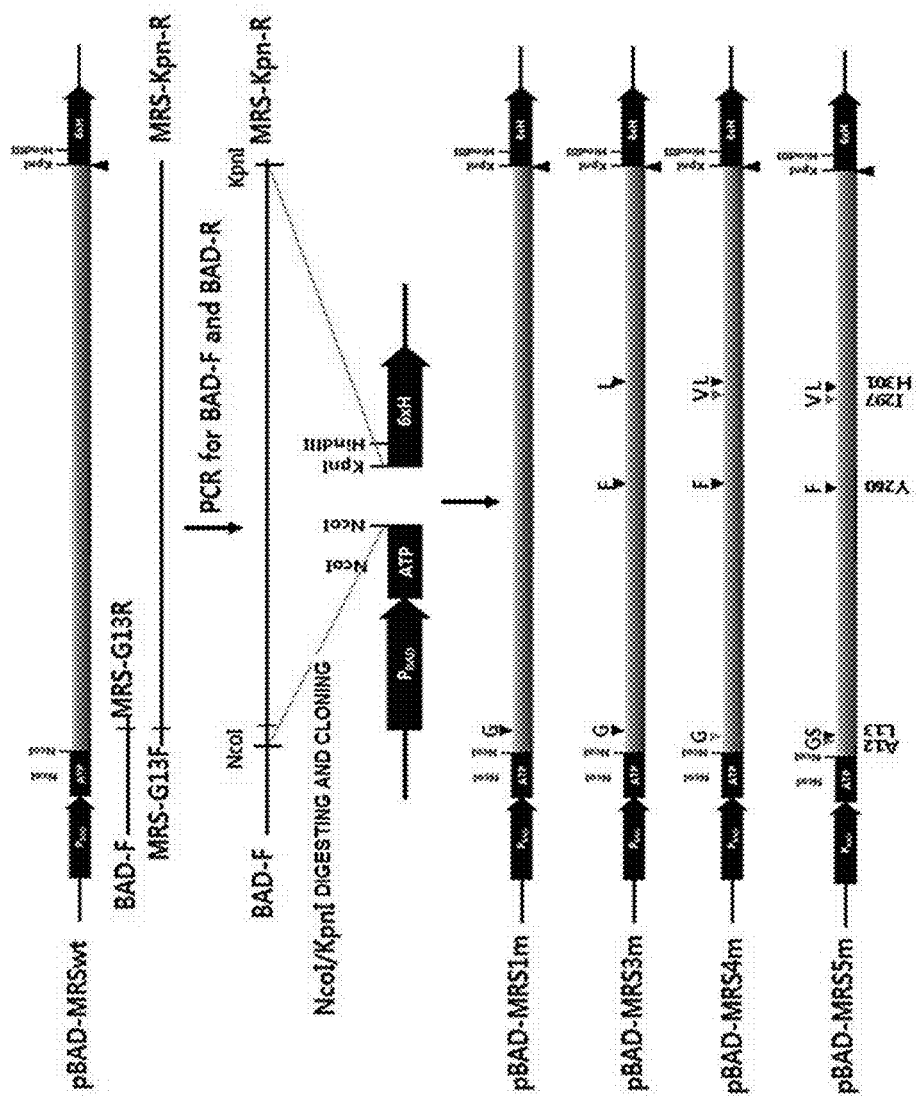
FIG. 4 is a mimetic diagram of preparing MRS variants through a wild-type MRS. A black reverse triangle represents the variants of positions of $13^{th}$, $260^{th}$, and $301^{st}$ which are known as existing methionine-binding sites and a gray reverse triangle represents the variants of positions of $12^{th}$ and $297^{th}$ targeted in the present invention. A black triangle represents a stop codon. A wide-type amino acid corresponding to each position is indicated below.

In order to prepare the MRS variant from the wild-type MRS, various point variants were prepared through a point mutagenesis method by using the pBAD-MRSwt vector as a template (see FIG. 4).

In detail, the primer used for preparing the MRS variant was summarized in Table 1.

The gene amplified through PCR as the configuration illustrated in FIG. 4 was purified and mixed by using a pair of primers including variant generation and used as the template and amplified through PCR as the BAD-F and MRS-Kpn-R primers again to obtain a product including a variant. Thereafter, the gene was cleaved with NcoI/KpnI and inserted into NcoI/KpnI of the pBAD/Myc-HisA vector to prepare pBAD-MRS1m. Other variants were prepared by the same method using a predetermined pair of primers to prepare pBAD-MRS3m, pBAD-MRS4m, and pBAD-MRS5m (see FIG. 4).

TABLE 1

Base sequence of primer using for cloning MRS and variant

| Name | Base sequence (5'→3') |
|---|---|
| MRS-Nco-F | AATTCCATGGCTCAAGTCGCGAA (SEQ ID NO: 13) |
| MRS-Kpn-R | CAGCGGTACCTTATTCTTTAGAGGCTTCCACC (SEQ ID NO: 14) |
| BAD-F | ATGCCATAGCATTTTTATCCA (SEQ ID NO: 15) |
| MRS-A12G-F | GACGTGCGGCCTGCCGTACGCTAACGGCTCAATCC (SEQ ID NO: 16) |
| MRS-A12G-R | ACGGCAGGCCGCACGTCACCAGAATTTTCTT (SEQ ID NO: 17) |
| MRS-L13G-F | GGGCCGTACGCTAACGGCTCAATC (SEQ ID NO: 18) |
| MRS-L13G-R | GATTGAGCCGTTAGCGTACGGCCCTGCGCACGTCACCAG (SEQ ID NO: 19) |
| MRS-AL/GS-F | GACGTGCGGCTCGCCGTACGCTAACGGCTCAATC (SEQ ID NO: 20) |
| MRS-AL/GS-R | ACGGCGAGCCGCACGTCACCAGAATTTTCTTCGC (SEQ ID NO: 21) |
| MRS-Y260E-F | ACCGATTGGCTTCATGGGTTCTTTCAAGAATCTGTGCGA (SEQ ID NO: 22) |
| MRS-Y260F | AAGAACCCATGAAGCCAATCGGTGCGTCCAGC (SEQ ID NO: 23) |
| MRS-I297V-F | GGTAAAGATGTTGTTTACTTCCTGAGCCTGTTCTGGCC (SEQ ID NO: 24) |
| MRS-I297V-R | GGCTCAGGAAGTAAACAACATCTTTACCGATGAAGTGGTACAG (SEQ ID NO: 25) |
| MRS-H301L-F | GATATTGTTTACTTCCTGAGCCTGTTCTGGCCTGC (SEQ ID NO: 26) |
| MRS-H301L-R | CAGAACAGGCTCAGGAAGTAAACAATATCTTTACC (SEQ ID NO: 27) |

MRS-Nco-F and MRS-Kpn-R are a primer set for amplifying sequences 1 to 548 of the MRS to introduce the amplified sequences to a pBAD/Myc-HisA vector.
MRS-A12G-F and MRS-A12G-R are a primer set for substituting alanine at the position of 12$^{th}$ with glycine.
MRS-L13G-F and MRS-L13G-R are a primer set for substituting leucine at the position of 13$^{th}$ with glycine.
MRS-AL/GS-F and MRS-AL/GS-R are a primer set for substituting alanine-glycine at the positions of 12$^{th}$ and 13$^{th}$ with glycine-serine.
MRS-Y260E-F and MRS-Y260E-R are a primer set for substituting tyrosine at the position of 260$^{th}$ with phenylalanine.
MRS-I297V-F and MRS-I297V-R are a primer set for substituting isoleucine at the position of 297$^{th}$ with valine.
MRS-H301L-F and MRS-H301L-R are a primer set for substituting histidine at the position of 301$^{st}$ with leucine.

[Example 4] Verification of Expression of pM-Labeled Protein in Methionine Heterotrophic *E. coli* (*E. coli* B834)

In order to verify the expression of the pM-labeled protein without expressing an external MRS, in *E. coli* B834 as methionine heterotrophic *E. coli*, the expression of pM-labeled EGFP, FIH, or GFP/FIH protein was verified.

In detail, in order to express the target protein with a 6×H tag, the pET-GFP, pET-FIH or pET-GFP/FIH vector prepared in Example 2 was transformed into the *E. coli* B834, and then colonies having resistance to kanamycin were selected and cultured for a day in an LB medium including 30 µg/ml kanamycin. Thereafter, the cultured *E. coli* was centrifuged at 2000×g for 15 to 20 minutes to be obtained, washed two times with M9B (48 mM Na$_2$HPO$_4$, 22 mM KH$_2$PO$_4$, 9 mM NaCl, and 19 mM NH$_4$Cl), and then diluted and dispersed by ⅕ in a M9BV+½ CMS-MET solution (M9B+0.4% glucose, 2 mM MgSO4, 0.1 mM CaCl 2, 0.05 mM MnCl 2, 0.1 M FeCl 3, 1 mg/ml thiamine, 0.2 mg/ml nicotinamide, 0.2 mg/ml folic acid, 0.2 mg/ml choline chloride, and 0.02 mg/ml riboflavine+375 µg/ml CSM-MET (a mixture of 19 amino acids except for methionine)). The dispersed *E. coli* was further cultured for 2 to 3 hours at 37° C. and then added with 375 µg/ml CSM-MET and 50 µg/ml methionine or pM to induce the protein expression for 12 to 16 hours at 20° C. with 1 mM isopropyl β-D-1-thiogalactopyranoside (IPTG). Thereafter, cells were centrifuged and washed with PBS, water was maximally removed by a micropipette, and then the wetted cells were diluted with distilled water at a concentration 100 mg/ml. Thereafter, 5 µl of the cells were mixed with a 2×SDS buffer solution of 5 µl and heated at 100° C. for 2 minutes to analyze the protein expression by SDS-polyacrylamide gel electrophoresis.

As a result, it was verified that the target protein was expressed in the methionine treatment, but the target protein was not nearly expressed in the pM treatment.

[Example 5] Verification of pM-Labeled 6×H-EGFP Protein Expression by MRS in *E. coli* B834

It was verified that the pM-labeled 6×H-EGFP protein was expressed in *E. coli* B834 by using 6×F-EGFP having a molecular weight of about 28 KDa and including 7 methionines in the molecule and the MRS variant prepared in Example 3.

In detail, pBAD-MRSwt or pBAD-MRS1m to pBAD-MRS5m, and pET-GFP prepared in Example 3 were transformed into *E. coli* B834, and then colonies having resistance to both ampicillin and kanamycin were selected and cultured for a day in an LB medium including ampicillin and kanamycin. The cultured *E. coli* was centrifuged at 2000×g for 15 to 20 minutes to be obtained and diluted and dispersed by ¹⁄₂₀ in a LB medium including ampicillin and kanamycin. The dispersed *E. coli* was cultured for 1 hour and then treated with 0.02% L-arabinose at 37° C. for 2 hours to express the wild-type MRS or the MRS variant. Thereafter, in order to express the EGFP as the target protein, the *E. coli* was washed two times with M9B and diluted by ½ to ⅓ in a M9BV+½ CMS-MET solution to induce the expression of the target protein by the same method as Example 4. Wetted cells which were obtained by centrifuge after culturing were diluted with water at a concentration of 100 mg/ml and then in 5 µm of the cells, the protein expression was analyzed by an SDS-polyacrylamide gel electrophoresis.

Figure 5:
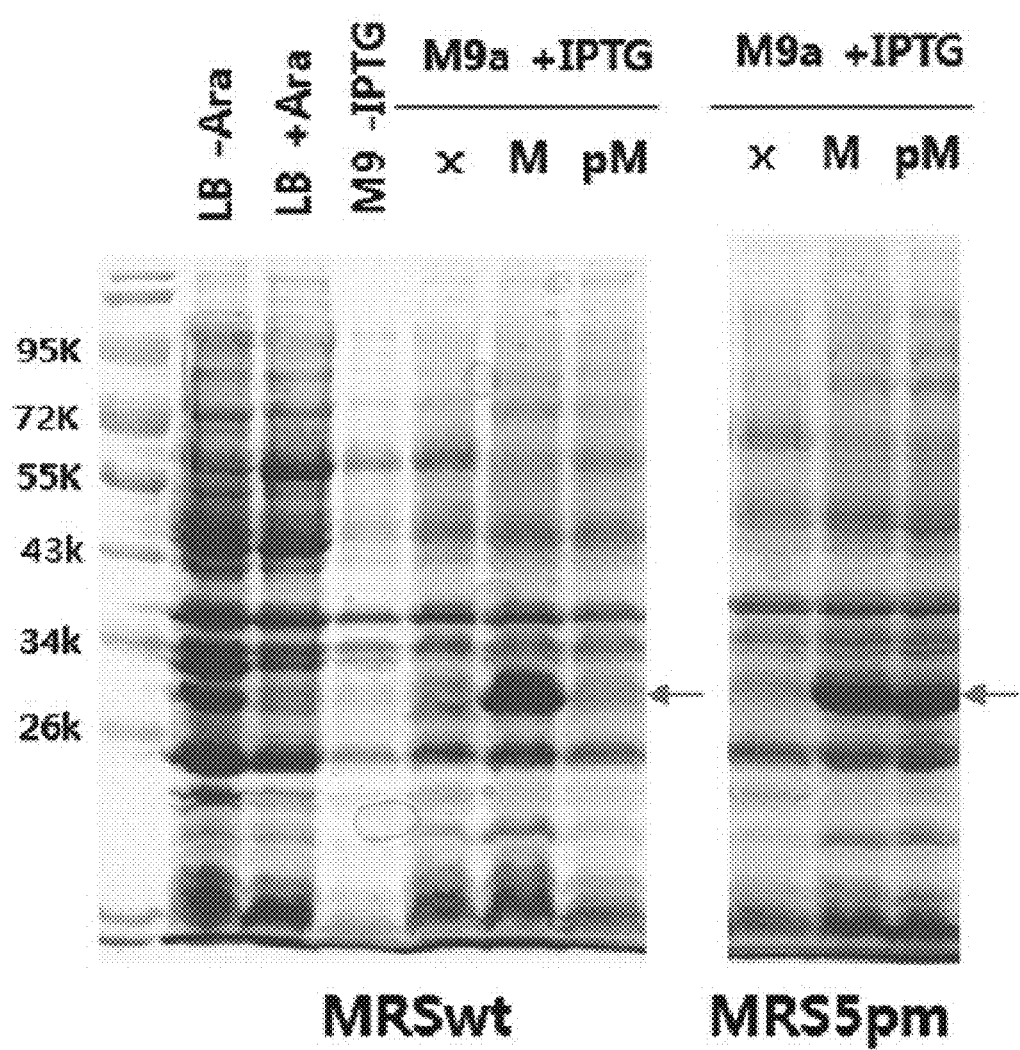
FIG. 5 illustrates an increase in expression of pM-labeled 6×H-EGFP by a MRS variant (MRS5pm). Ara represents 0.02% L-arabinose, IPTG represents 1 mM IPTG, and M9a represents M9BV+CMS-MET. X represents a case where *E. coli* is cultured in a medium without a methionine nutrient, M represents a case where *E. coli* is cultured in a medium with methionine, and pM represents a case where *E. coli* is cultured in a medium with a methionine nutrient. An expressed 6×H-EGFP protein was illustrated by a red arrow.

As a result, as illustrated in FIG. 5, like the case where the external MRS was not expressed, it was verified that under a condition in which the wild-type MRS was expressed, the high protein expression in the methionine treatment was shown, but the EGFP protein in the pM treatment was not nearly expressed. Further, it was verified that in the MRS1pm and MRS3pm variants which cause the mutation at the positions of 13$^{th}$, 260$^{th}$, and 301$^{st}$ which were previously known, the protein expression by pM was not increased like the wild-type MRS. However, in the case of expressing the MRS5pm variant, it was verified that the 6×H-EGFP protein was expressed even when the pM was treated like the case where the methionine was treated (see FIG. 5). Further, it was verified that the 6×H-EGFP protein was not expressed by IPTG when the methionine or pM was not treated, and thus the pM was included in the 6×H-EGFP expressed in the pM treatment (see FIG. 5).

Figure 6:
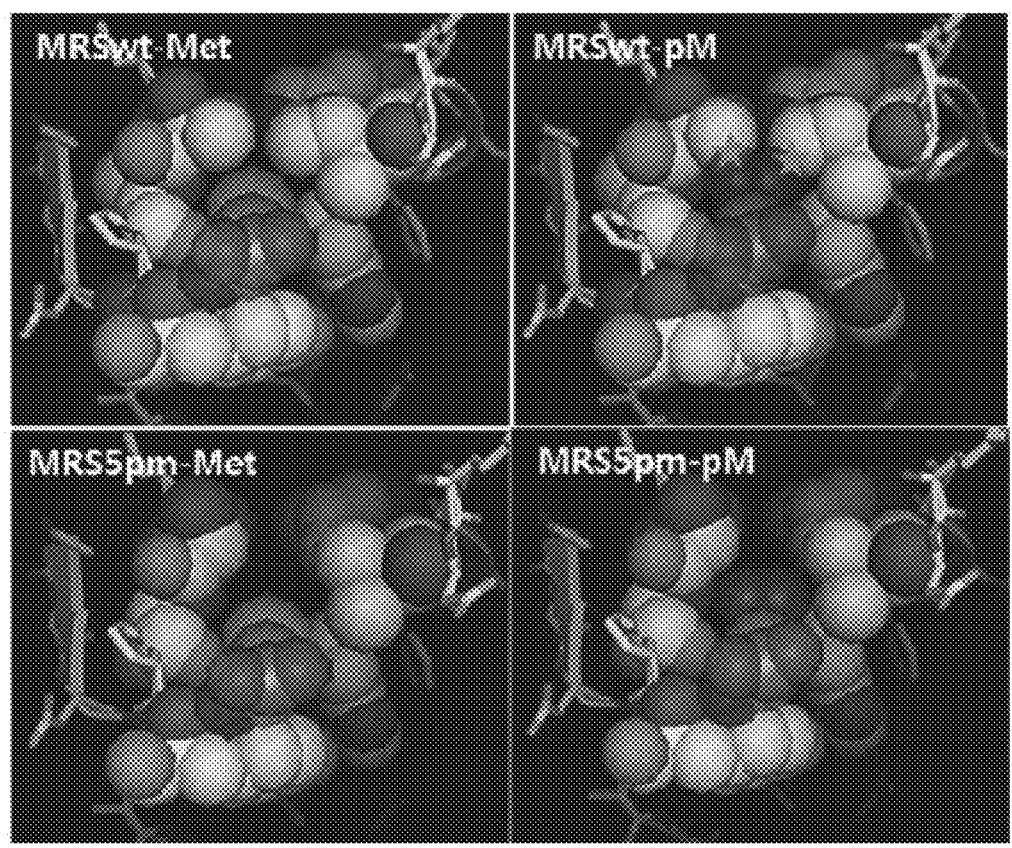
FIG. 6 is a diagram of expecting a binding structure of the wide-type MRS or the MRS5pm variant and methionine (Met) or pM. A red star of MRSwt-pM illustrates that when pM approaches a binding region of the wide-type MRS so that the wide-type MRS and the pM are bound with each other, molecular collision occurs and the binding is not easy.

The result shows that as illustrated in FIG. 6, the binding of the wild-type MRS and the methionine is easy, but due to the structure of the pM having a diazirine group which further protrudes than methionine, since the MRS having Ala12 and Ile297 such as the wild-type MRS or the MRS1pm and MRS3pm variants has an insufficient space in which the pM may approach the ligand binding region, the binding of the pM is difficult. Meanwhile, it was verified that the MRS5pm variant had an effect of facilitating the approach of the pM to the ligand binding region of the MRS by substituting Ala12 and Ile297 residues with glycine and valine, respectively, in order to remove a methyl group (see FIG. 6). Further, it was verified that an effect of introducing the pM to the target protein such as 6×H-EGFP was improved by substituting Leu13, Tyr260 and His301 as binding regions of an existing known substrate with serine, phenylalanine and leucine, respectively, in order to optimize the binding of the pM (see FIG. 6).

[Example 6] Expression of pM-Labeled 6×H-FIH Protein by MRS in *E. coli* B834

The pM-labeled 6×H-FIH protein was expressed in *E. coli* B834 by using 6×FIH having a molecular weight of about 45 KDa and including 10 methionines in the molecule and the MRS variant prepared in Example 3.

In detail, after pBAD-MRSwt or pBAD-MRS1m to pBAD-MRS5m and pET-FIH were transformed into the *E. coli* B834, the MRS and FIH proteins were expressed by the same method as Example 5. After culturing, wetted cells which were obtained by centrifuge were diluted with water at a concentration of 100 mg/ml and then in 5 µl of the cells, the protein expression was analyzed by an SDS-polyacrylamide gel electrophoresis.

Figure 7:
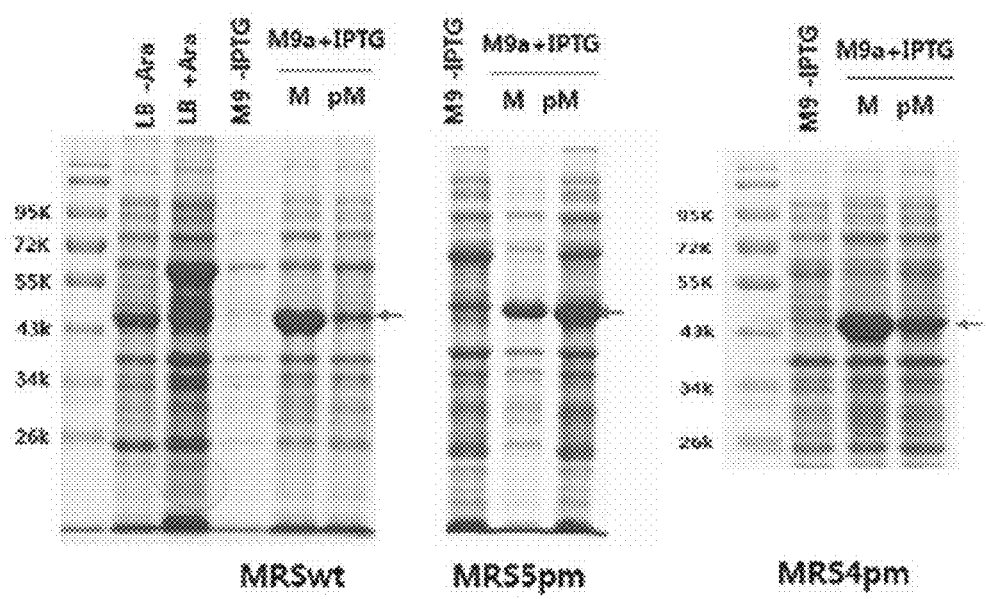
FIG. 7 illustrates an increase in expression of pM-labeled 6×H-FIH by a MRS variant (MRS5pm). Ara represents 0.02% L-arabinose, IPTG represents 1 mM IPTG, and M9a represents M9BV+CMS-MET. M represents a case where *E. coli* is cultured in a medium with methionine, and pM represents a case where *E. coli* is cultured in a medium with a methionine nutrient. An expressed 6×H-EGFP protein was illustrated by a red arrow.

As a result, as illustrated in FIG. 7, when the MRS5pm variant was expressed, the 6×H-FIH protein was significantly expressed in the pM treatment as compared with the methionine treatment. Further, when the MRS4pm variant was expressed, the pM-labeled protein was expressed in the 6×H-FIH, but the pM-labeled protein was expressed less than the case when the wild-type and MRS5pm variants were expressed (see FIG. 7). Since the MRS4pm variant was a variant substituted with only four amino acid residues except of substituting Leu13 with serine among five amino acid residues substituted in the MRS5pm variant, it is important to substitute the Leu13 residue with serine in the expression of the pM-labeled protein by the MRS variant.

[Example 7] Partial Separation and Purification of pM-Labeled 6×H-EGFP and 6×H-FIH Proteins In order to purify the expressed pM-labeled protein, a pM-labeled 6×H-targeted protein was partially separated and purified through an Ni-NTA-agarose chromatography.

In detail, in order to separate the pM-labeled 6×H-targeted protein, *E. coli* expressing the pM-labeled protein including the MRS5pm variant cultured in Example 5 or Example 6 was centrifuged to obtain cells. Thereafter, 100 ml of a culture solution was dispersed in 1 to 2 ml of a buffer solution for cell destruction (20 mM Tris-HCl, 300 mM NaCL, 2 mM 2-mercaptoethanol, 1 mM PMSF, and 5% glycerol) and then crushed with ultrasound. The crushed solution was centrifuged at 15,000 rpm for 20 minutes to obtain a supernatant and partially separated and purified by a Ni-NTA-agarose chromatography.

Figure 8:
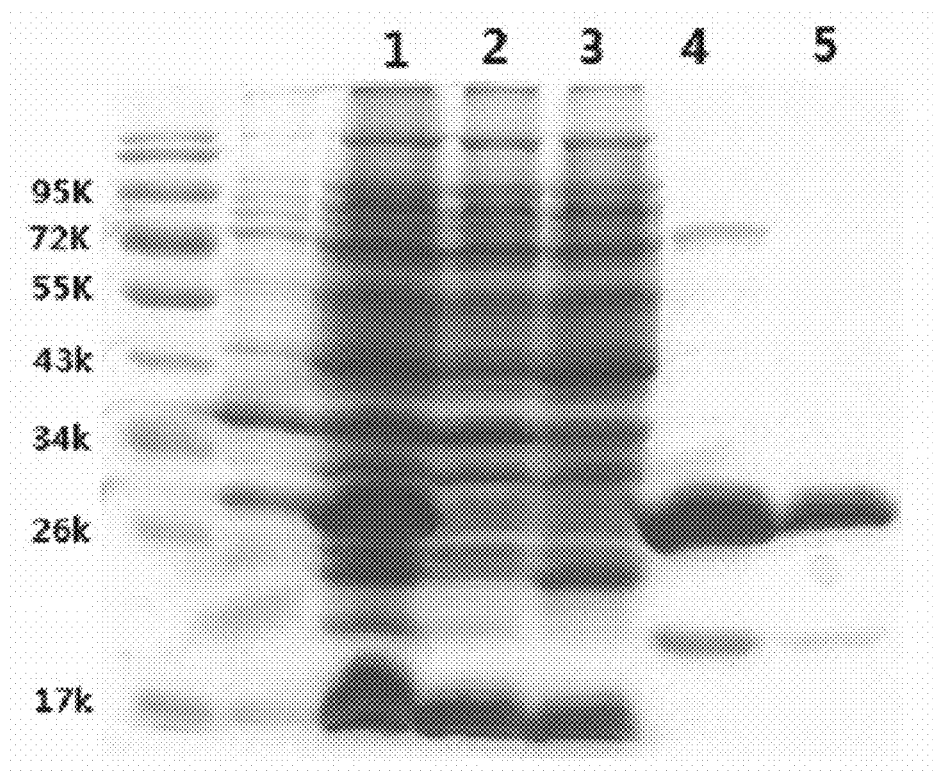
FIG. 8 illustrated purification of the pM-labeled 6×H-EGFP. 1 represents a supernatant obtained by ultrasonic-crushing and centrifuging cultured *E. coli*, 2 represents a unpurified release solution which is not bound with a chromatography and flows trough, 3 represents a release solution washed with 30 mM histidine, and 4 and 5 represent 6×H-EGFP which is released with 150 mM imidazol, obtained and purified.

As a result, as illustrated in FIG. 8, it was verified that the 6×His-tagged target protein was partially separated and purified at a concentration of 150 mM imidazole by a step gradient Ni-NTA-agarose chromatography (see FIG. 8).

[Example 8] Analysis of Photoactivatable Covalent Bond of pM-Labeled 6×H-EGFP and 6×H-FIH Proteins In order to verify photoactivity of the pM labeled in the expressed target protein, the photoactivatable covalent bond of the expressed target protein was analyzed.

In detail, it was verified that dimers between proteins were formed by irradiating UV having a wavelength of 365 nm to the pM-labeled protein which was partially separated and purified in Example 7.

As a result, it was verified that dimers between EGFP proteins which were known to be present as a monomer were not formed. Further, as illustrated in FIG. 9, it is known that 6×H-FIH forms the dimer with a C-terminal, three methionine residues are present at the dimer formation region, and two residues thereof has a structure which is very close to corresponding FIH methionine residues (see FIG. 9). However, it was verified that the FIH proteins was also present as a precipitant when subject to UV irradiation in the culture of the present invention and an induction condition by IPTG unlike the IPTG induction condition (Lee, et al., Biol Chem, 278, 7558-63, 2003) in the LB medium.

[Example 9] Partial Separation and Purification and Analysis of Photoactivatable Covalent Bond of pM-Labeled 6×H-GFP/FIH Protein In order to overcome that the photoactivatable covalent bond was not formed in the protein of Example 8, a GFP/FIH protein expressed by binding the EGFP to the amino terminal of the FIH was expressed in *E. coli*.

In detail, the pBAD-MRS5m and the pET-GFP/FIH prepared in Example 2 were transformed into *E. coli* B834 and then the MRS variant and the GFP/FIH protein were expressed by the same method as Example 5. Thereafter, the pM-labeled 6×H-GFP/FIH protein was partially separated and purified through the Ni-NTA-agarose chromatography by the same method as Example 7, a dimer between the proteins was formed by irradiating UV having a wavelength of 365 nm, and the formation of the dimer between the proteins was verified through coomassie brilliant blue R-250 staining and western blotting analysis after being deployed in an SDS-polyacryl amide gel.

For the western blotting, after SDS-PAGE, the protein moved to a nitrocellulose (NC) membrane to be sequentially bound with an anti-mouse IgG goat antibody (milipore, USA) which was bound with a 6×H-specific mouse monoclonal antibody (Aviva Systems biology, USA) and horseradish peroxidase. Thereafter, the protein was treated with an Amersham ECL western blotting detection reagent (GE Healthcare, USA) and verified.

As a result, as illustrated in FIG. 10, since a small amount of 6×H-GFP/FIH protein was separated and purified (FIG. 10A) and 6×H was present only in the GFP-FIH which was the protein into which the tag was artificially inserted, the protein was not completely purified and thus several protein bands were present at a position of 72 KDa, but the band responding to the 6×H-specific antibody may be only one. In addition, it was verified that the pM-labeled 6×H-GFP/FIH protein formed the dimer when irradiating UV having a wavelength of 386 nm through western blotting (see FIG. 10B).

[Example 10] Preparation of Protein G Vector for Introducing Methionine

In order to obtain the pM-labeled protein G using the MRS obtained by the method disclosed in Example 3, first, a vector including one or two protein G motifs in the pET-28at vector prepared in Example 1 was prepared.

In detail, pET-2×FcBP (Jung et al., Anal Chem, 81, 936-42, 2009) was subject to polymerase chain reaction (PCR) by using a primer of the following Table 2 as a template to obtain a PCR product in which a third immunoglobulin G-binding region C3 (PG-C3, Olsson et al., Eur J Biochem, 168, 319-24, 1987, SEQ ID NO: 4) of one or two protein G was included. Next, the PCR product was cleaved with restriction enzymes BamHI and XhoI to be cloned at a BamHI/XhoI site of the pET-28at vector (see FIG. 1) and plasmids including one or two PG-C3s were called pET-PG and pET-2×PG, respectively (see FIG. 11).

TABLE 2

| Primer | Sequence (5'→3') |
|---|---|
| PG-Bam-F forward primer | ATAGGATCCTGCTGCGGCGGGACAACTTACAAAC TTGTTATT (SEQ ID NO: 28) |
| PG-Xho-R reverse primer | GCGCCTCGAGTTATTCAGTTACCGTAAAGGTC (SEQ ID NO: 29) |

[Example 11] Preparation of Methionine-Substituted Protein G Plasmid

In order to introduce the proteins into the positions of $32^{nd}$, $35^{th}$, and $40^{th}$ based on the binding structure of the protein G and the antibody (Sauer-Eriksson et al., Structure, 3, 265-78, 1995), a variant protein G plasmid was prepared by substituting PG-C3 in the pET-2×PG plasmid including two PG-C3 motifs and the pET-PG plasmid including one PG-C3 motif which were obtained by the method disclosed in Example 10 with methionine.

In detail, the numbers of amino acid residues substituted for introducing the methionine were set base on the PG-C3 motif and the residues substituted by Met were selected based on the tertiary binding structure between the protein G and the antibody. Next, in order to prepare the variant, the PCR was performed by using a primer set in the following Table 3 like a mimetic diagram of FIG. 3. First, in order to substitute glutamine Gln32 at the position of $32^{nd}$ by methionine, PCR was performed by using ET-Xba-F/PG-Q32M-R and PG-Q32M-F/Ins-Cla-R among the primer sets in the following Table 3 using pET-2×PG obtained by the method disclosed in Example 10 as the template to obtain each PCR product. The obtained PCR product was mixed and PCR DNA was obtained by using ET-Xba-F/Ins-Cla-R among the primer sets in the following Table 3 using the PCR product as a template and then cleaved with BamHI and ClaI and purified to obtain insert 1 DNA. Next, the PCR was performed above by using Ins-Cla-F/PG-Q32M-R and PG-Q32M-F/ET-R among the primer sets in the following Table 2 using pET-2×PG as a template to obtain each PCR product. The obtained PCR product was mixed and PCR DNA was obtained by using Ins-ClaI-F/ET-R among the primer sets in the following Table 3 using the PCR product as a template and then cleaved with ClaI and XhoI and purified to obtain insert 2 DNA. Thereafter, the insert 1 DNA and the insert 2 DNA were mixed and cloned in a BamHI/XhoI site of the pET-28at to obtain a pET-2×PG1m plasmid. Next, the PCR was performed by the above method using the pET-2×PG2m plasmid as a template to prepare pET-2× PG2m in which aspartic acid Asp40 at the position of 40$^{th}$ of the PG-C3 motif and Gln32 were substituted by Met. Further, the PCR was performed by the above method using the pET-2×PG2m plasmid as a template to prepare pET-2× PG3m in which asparagine Asn37 at the position of 37$^{th}$ was substituted by arginine (Arg) and Asp40 and Gln32 were substituted by Met. Thereafter, the PCR was performed by the above method using the pET-2×PG3m plasmid as a template to prepare pET-2×PG4m in which asparagine Asn35 at the position of 35$^{th}$, Asp40, and Gln32 were substituted by Met and Asn37 was substituted by Arg (see FIG. 12).

TABLE 3

| Primer set | Sequence (5'-3') |
|---|---|
| PG-Bam-F | ATAGGATCCTGCTGCGGCGGGACAACTTACAAAC TTGTTATT (SEQ ID NO: 30) |
| PG-XhoI-R | GCGCCTCGAGTTATTCAGTTACCGTAAAGGTC (SEQ ID NO: 31) |
| PG-Q32M-F | AAAGCCTTCAAAATGTACGCTAACGAGAACGG (SEQ ID NO: 32) |
| PG-Q32M-R | GTTAGCGTACATTTTGAAGGCTTTTTCTGCAGTTT CTGC (SEQ ID NO: 33) |
| PG-D40M-F | GACAACGGTGTTATGGGTGTTTGGACTTATGATG (SEQ ID NO: 34) |
| PG-D40M-R | CCAAACACCCATAACACCGTTGTCGTTAGCG (SEQ ID NO: 35) |
| PG-N37R-F | GCTAACGACCGCGGTGTTATGGGTGTTTGG (SEQ ID NO: 36) |
| PG-N37-R | CATAACACCGCGGTCGTTAGCGTACATTTT (SEQ ID NO: 37) |
| PG-35, 37-F | GCTATGGACCGCGGTGTTATGGGTGTTTGG (SEQ ID NO: 38) |
| PG-35, 37-R | CATAACACCGCGGTCCATAGCGTACATTTTGAAG GC (SEQ ID NO: 39) |
| Ins-Cla-F | GAAGTGATCGATGCGTCTGAATTA (SEQ ID NO: 40) |
| Ins-Cla-R | TAATTCAGACGCATCGATCACTTC (SEQ ID NO: 41) |
| ET-Xba-F | TTCCCCTCTAGAAATAATTTTGTTTAAC (SEQ ID NO: 42) |
| ET-R | TTATGCTAGTTATTGCTCAGCGGTGGCAG (SEQ ID NO: 43) |

Further, in order to prepare the variant with one protein G motif, as illustrated in the mimetic diagram of FIG. 13, the PCR was performed with ET-Xba-F/PG-XhoI-R among the primer sets in the Table 3 using the pET-2×PG1m, pET-2× PG2m, pET-2×PG3m, and pET-2×PG4m variant plasmids obtained by the above disclosed method as a template to obtain a PCR DNA including one PG motif. The obtained PCR DNA was purified, cleaved by using BamHI and XhoI, and then cloned to the BamHI/XhoI site of the pET-28at.

The PG variant plasmids were called pET-PG1m, pET-PG2m, pET-PG3m, and pET-PG4m (see FIG. 13).

[Example 12] Preparation of pM-Labeled Protein G Expression Vector and Transformant by MRS Variant In order to express the pM-labeled protein G variant, the pBAD-MRS5m plasmid prepared in Example 3 and the plasmid encoding the PG-C3 variants obtained by the method disclosed in Example 11 were transformed into Met auxotroph E. coli B834. Next, transformed E. coli colonies including all of the MRS5m and the PG-C3 variant plasmids were selected in an LB solid medium including 100 μg/ml ampicillin and 50 μg/ml kanamycin, suspended in an LB liquid medium, and cultured for 24 hours. Next, the two liquids were diluted to a volume of ⅒ to 1/20 to be cultured in LB liquid medium including ampicillin and kanamycin for 1 to 2 hours and then treated with 0.02% L-arabinose at 37° C. for 2 hours to express MRS5m. Next, the MRS5m expressed E. coli was washed two times with a M9B solution (48 mM Na$_2$HPO$_4$, 22 mM KH$_2$PO$_4$, 9 mM NaCl, and 19 mM NH$_4$Cl) and diluted to ½ to ⅓ in a M9BV+½ CMS-MET solution [M9B+0.4% glucose 2 mM MgSO$_4$, 0.1 mM CaCl$_2$, 0.05 mM MnCl$_2$, 0.1 M FeCl$_3$, 1 mg/ml thiamine, 0.2 mg/ml nicotinamide, 0.2 mg/ml folic acid, 0.2 mg/ml choline chloride, and 0.02 mg/ml riboflavine+375 μg/ml CSM-MET (a mixture of 19 amino acids except for methionine)]. Next, the E. coli was further cultured at 37° C. for 1 to 2 hours or at 18° C. for 3 hours to make a deficiency of Met and added with 375 μg/ml CSM-MET to be 50 μg/ml methionine or 50 to 100 μg/ml pM to induce the protein expression for 16 to 20 hours at 18° C. with 1 mM isopropyl β-D-1-thiogalactopyranoside (IPTG). The expressed proteins were called 6H-2×PG1m, 6H-2×PG2m, 6H-2×PG3m1, 6H-2×PG3m2, and 6H-2×PG4m in the case of having two PG-C3 motifs and 6H-PG1m, 6H-PG2m, 6H-PG3m1, 6H-PG3m2, and 6H-PG4m in the case of having one PG-C3 motif, respectively.

As a result, as illustrated in FIG. 14, it was verified that the expression of the pM-labeled 6H-2×PG2m was increased by the MRS5m and the protein expression during the pM single treatment by normal MRS (MRSwt) was very low, but the expression of the protein was significantly increased by the MRS5m even in the pM single treatment similarly to the Met treatment (see FIG. 14). Further, it was verified that when the pM treatment concentration was increased two times to 100 μg/ml, the protein expression amount was significantly increased together, and even in other Met variants, the expression of the pM-labeled protein by MRS5m was increased like the 6H-2×PG2m.

[Example 13] Partial Separation and Purification and Mass Spectrometry of Protein G Variant The protein G variants expressed by the method disclosed in Example 12 were expressed in a dissolved form and 6×H groups were bound with amino terminals of the proteins to be partially purified by Ni-NTA-agarose (Qiagen, USA) chromatography.

In detail, the transformed E. coli in which 6H-2×PG1m, 6H-2×PG2m, 6H-2×PG3m1, 6H-2×PG3m2 and 6H-2× PG4m, and 6H-PG1m, 6H-PG2m, 6H-PG3m1, 6H-PG3m2 and 6H-PG4m were expressed by the method disclosed in Example 12 was centrifuged, dispersed in a 1 to 2 ml of a buffer solution for cell destruction (20 mM Tris-HCl, 500 mM NaCL, 2 mM 2-mercaptoethanol, 1 mM PMSF, and 5% glycerol) per 100 ml culture solution, and crushed with an ultrasonic wave. The crushed solution was centrifuged at 15,000 rpm for 10 to 20 minutes and then a supernatant was collected and partially separated and purified by the Ni-NTA-agarose chromatography. The purified supernatant verified whether to express the 6H-2×PG1m, 6H-2×PG2m, 6H-2×PG3m1, 6H-2×PG3m2 and 6H-2×PG4m, and 6H-PG1m, 6H-PG2m, 6H-PG3m1, 6H-PG3m2 and 6H-PG4m protein G variants by performing the SDS-PAGE.

As a result, as illustrated in FIGS. 15 and 16, it was verified that most of 6H-2×PG2m was released from 150 mM imidazole in the step gradient, and thus, other variants were partially purified under the same condition. Interestingly, it was verified that the purified Met or the pM-labeled 6H-2×PG2m formed an oligomer such as a dimer, a trimer, and a tetramer of which an amount is small in addition to a monomer (see FIG. 15). The result is considered to induce the formation of the oligomer which is a stable form according to a heating condition under the SDS presence by introducing Met which is more hydrophobic than an original amino acid. However, the formation of the dimer and the oligomer of PG-C3 may have a bad effect on capturing the antibody to ultimately have high orientation. It is reported that since Asn37 is important in binding to a CH1 site of Fab of the antibody, but does not influence the Fc site binding, Fab binding may be minimized by substituting Asn37 by tyrosine (Tyr) (Jung et al., Anal Chem, 81, 936-42, 2009). Meanwhile, it was verified that even though Asn37 of the 6×H-2×PG2m was substituted by Tyr, the formation of the oligomers was not reduced, but in the case of the 6H-2×PG3m in which Asn37 was substituted by Arg, the formation of the oligomers was reduced (FIG. 16).

Further, LC/MS/MS mass spectrometry was performed with respect to cleaved peptides extracted after tyrosine enzyme decomposition by extracting the monomers and the dimers on the SDS, and as a result, it was verified that the peptides included PG-C3 sequences and thus the band at the dimer position was the protein G derivative. Further, it was verified that the highest pM labeling rate was exhibited to 50 to 70% in the case of the deficiency of methionine at 18° C.

[Example 14] Verification of Covalent Bond Between Protein G Variant and Immunoglobulin G (IgG)

In order to verify the covalent bond between the pM-labeled protein G variant and the immunoglobulin, SDS-PAGE analysis and covalent bond formation analysis were performed.

In detail, the 6H-2×PG4m protein G variant purified by the method disclosed in Example 13 and anti-EGFR human monoclonal antibody (Erbitux, Merck, USA) or Fc fraction (abcam, USA) were mixed to perform the SDS-PAGE after irradiating 365 nm UV for 30 minutes in ice and observe whether the covalent bond is present (see FIG. 17).

Further, the 6H-PG3m or 6H-PG4m protein G variant purified by the method disclosed in Example 13 and anti-EGFR human monoclonal antibody or the Fc fraction were mixed to perform SDS-PAGE after irradiating 365 nm UV for 30 minutes in ice and observe whether the covalent bond is present and measure the density of bands by an image J program and calculate IgG heavy covalent binding rate and Fc covalent binding rate were calculated (FIG. 18).

IgG heavy covalent binding rate (%)=[$H$-$PG$ density/($H$-$PG$ density+$H$ density)×100]; and Fc covalent binding rate=[$Fc$-$PG$ density/($Fc$-$PG$ density+$Fc$ density)×100].

Further, according to presence of 2-mercaptoethanol, whether the covalent bond between the 6H-PG3m or 6H-PG4m protein G variant and the Fc fraction is present was observed and the covalent binding rate was calculated as described above (FIG. 19).

As a result, as illustrated in FIG. 17, the covalent bond between the PG-C3 variant and the IgG is formed only when irradiating UV to a mixed solution of the pM-labeled PG-C3 variant and the IgG or the Fc, and it was verified that the protein G variant had specificity to the IgG heavy chain by verifying that two IgG heavy chains (H) or Fc sites were bound with one protein G molecule protein G concentration-dependently (see FIG. 17). Further, the covalent bond between the pM-labeled PG-C3 and the IgG or the Fc was further formed in the 6H-2×PG2m than 6H-2×PG1m in proportion to the number of methionine (Met) substituents, and the 6H-2×PG3m introducing Arg at the position of $37^{th}$ had similar covalent binding capacity as compared with the 6H-2×PG2m. The 6H-2×PG4m in which methionine was further introduced into the position of $35^{th}$ of the 6H-2×PG3m had the highest covalent binding formation than the 6H-2×PG3m. In the case of having two PG-C3 sites such as 6H-2×PG3m and 6H-2×PG4m, it was verified that the covalent bond between two-molecule IgG heavy chain per molecule and Fc site was formed.

Further, as illustrated in FIG. 18, the 6H-PG3m and the 6H-PG4m having one PG-C3 site was bound with 1-molecule antibody heavy chain, and as a result of analyzing the covalent bond formation capacity by UV irradiation, it was verified that the covalent bond formation capacity of 6H-PG4m having three methionines was higher than that of the 6H-PG3m having two methionines as expected. It was verified that when 2-mercaptoethanol was present, the pM-labeled 6H-PG3m formed a covalent bond with the heavy chain with a covalent bond rate of 41.5±1.8% and the pM-labeled 6H-PG4m with a covalent bond rate of 53.0±1.0%. Further, it was verified that the pM-labeled 6H-PG3m and 6H-PG4m formed the covalent bond with the human Fc fraction and the covalent bond rate was similar to the binding rate for the heavy chain of IgG with 35.8±1.7% and 52.1±1.0% (see FIG. 18).

Further, since IgG 1 molecule had 2-molecule protein G binding region, in the SDS-PAGE under the presence of the double 2-mercaptoethanol (2ME), when formation probability of the covalent bond between the protein G and the IgG was 50%, probability of the covalent bond between one or more proteins G and IgG was 75%, and when the formation probability of the covalent bond was 35%, the probability of the covalent bond was 58%. As illustrated in FIG. 19, it was verified that the 6H-PG3m had a binding rate of 35.2% (+2ME) and 57.4% (−2ME) and the 6H-PG4m had a binding rate of 48.2% (+2ME) and 68.5% (−2ME), and accordingly, it was verified that the result was close to a theoretical calculation value.

[Example 15] Verification of Substitution Inhibiting Capacity of Antibody in Blood by Covalent Bond Between IgG and Protein G The protein G is very useful for preparing various antibody chips, but reversibly substituted by the IgG in the blood when treating the blood sample and the covalent bond therebetween may be suppressed. Accordingly, in order to analyze the substitution inhibiting capacity of the antibody in the blood by the covalent bond between the IgG and the protein G, SDS-PAGE, coomassie staining, and western blotting were performed.

In detail, 500 μg biotin-N-hydroxysuccinimide (NHS) was bound with 5 mg human IgG (Erbitux) balanced in PBS for 1 hour and then dialyzed to prepare a biotinylated IgG (bIgG). Next, the prepared bIgG 20 μg, 10 μg Met, or the pM-labeled 6H-PG4m were mixed to perform the SDS-PAGE after UV irradiation like Example 14.

As a result, it was verified that the prepared biotinylated IgG and the pM-labeled 6H-PG4m formed the covalent bond after irradiating the UV.

Further, the bIgG 20 μg, 10 μg Met, or the pM-labeled 6H-PG4m were bound with 10 μl Ni-NTA-agarose bead (Quiagen, Germany) under the presence of 30 mM imidazole and then the bead was washed with a washing buffer solution 20 mM Tris-HCl, 300 mM NaCl and 30 mM imidazole, pH 7.5) twice and with TBS (20 mM Tris, 150 mM NaCl and 0.05% Tween 20, pH 7.5) twice, and then treated with human serum (Sigma-Aldrich, USA) and 2% bovine serum albumin (BSA) solution by 150 μl twice for 2 hours. Thereafter, the bead was washed with the washing buffer solution and the TBS three times again and then released with 30 μl release buffer solution (20 mM Tris-HCl, 300 mM NaCl and 150 mM imidazole, pH 7.5). The released bIgG was separated in a SDS-PAGE gel by electrophoresis and stained with coomassie brilliant blue R-250 (see left of FIG. 20) or moved to a nitrocellulose membrane and visualized by using streptavidin-peroxidase (see right of FIG. 20).

As a result, as illustrated in FIG. 20, as a result of analyzing the overall protein shape by coomassie staining, it was verified that in a light chain (bL) band of IgG, and pM labeling and UV irradiation groups, a change by serum treatment was slight, but in other groups, the change was almost gone and a combination bH-PG of the heavy chain (bH) of bIgG and the 6H-PG4m was not nearly reduced by the serum treatment (see left of FIG. 20). Further, it was verified that even in the shape analyzed by western blotting, even though signals of the bH and bH-PG bands were slight, but similarly, in the pM-labeled and UV-irradiated groups, the bL, bH and bH-PG bands are almost not influenced by the serum treatment, but in other groups, the bIgG bound to the protein G was disassociated 80% or more by the serum treatment (see right of FIG. 20).

Accordingly, through the result, it can be seen that an IgG-protein G variant covalent conjugate may be used for developing an antibody chip for analyzing a blood sample and the like, and further, may be used for preparing a target-oriented nanoparticle delivery system for antibody-labeled intravenous injection.

[Example 16] Analysis of Protein Detection Capacity in Blood of Covalent Conjugate of IgG and Protein G by Immunoprecipitation The protein G is very useful for manufacturing various antibody chips, but the protein G is reversibly disassociated by the antibody in the blood when treating the blood sample and thus the protein G may not be used for detecting the protein in the blood and capturing the cells. Accordingly, in order to verify availability for detecting the protein in the blood of the pM-labeled protein variant, immunoprecipitation was performed.

In detail, for immunoprecipitation, 10 μg pM-labeled 6H-PG4m was attached to 10 μl Sulfo Link-coupling resin (Thermo Sci, USA) and then treated with 2% BSA for 1 hour. Next, the resin was washed with a washing buffer solution three times and then treated with 20 μg anti-HER2 human monoclonal antibody (Herceptin), and a part was irradiated by 365 nm UV for 30 minutes to induce a covalent bond. 5 μg 6H-HER2 protein (Sino Biological Inc, China) was mixed with a human serum and 2% BSA 100 μl and then binding with the antibody was induced for 1 hour in the pM-labeled 6H-PG4m resin. Next, the resin was washed with a washing buffer solution of 200 μl four times and the solution of the resin was sufficiently removed, and then the resin was released with a 1% SDS solution. An amount of HER2 in the released solution are separated in a SDS-PAGE gel by electrophoresis and visualized by using Coomassie brilliant blue R-250 staining (see left of FIG. 21) or an anti-6×His mouse antibody (Abcam, USA) and an peroxidase-labeled anti-mouse-IgG goat antibody (Life Technologies, USA) after moving to a nitrocellulose membrane (see right of FIG. 21).

As a result, as illustrated in FIG. 21, overall, in the immunoprecipitated 6H-HER2, it was verified that a high recovery rate after immunoprecipitation of 20 to 30% was exhibited regardless of human serum treatment in the group irradiating UV, and interestingly, in the case of treating the human serum, a high recovery rate was shown to about 40%. Meanwhile, in a group which is not irradiated with UV, even in a group which is not treated with the human serum, the recovery rate was shown less than 10%, and in the case of treating the human serum, the recovery rate of less than 2% was shown. As a result, it was verified that when the antibody was covalent-bound with the protein G by UV irradiation, it was very useful in analyzing the antigen in the blood (see FIG. 21).

[Example 17] Verification of Analysis Capacity of Antigen in Blood of Protein Chip in which Antibody is Covalent-Bound with Protein G A highly oriented antibody may be used as a tool which is very useful in antigen analysis in the blood sample of the bound protein chip. Accordingly, the analysis of the antigen in the blood sample was performed by covalent-binding a photoactivatable protein G on a slide glass and immobilizing the antibody to have high orientation by UV irradiation.

In detail, first, six wells of 12×8 mm were made on a slide glass (CEL Vantage Aldehyde Microarray Slides; Arrayit Co., USA) activated with an aldehyde group for detecting the antigen, 100 μl of 50 mM N-(2-aminoethyl)maleimide hydrochloride (Tokyo Chemical Ind, Japan) dissolved in PBS was added in each well and then bound with each other for 1 hour, and then a free aldehyde group was removed by treating 150 μl of 100 mM Tris-HCl, pH 7.5 and washed three times with TBST (20 mM Tris-HCl, 150 mM sodium chloride, 0.05% Tween 20, pH 7.5). Next, 6H-2×PG4m and 6H-PG4m were dissolved in the PBS at concentrations of 1 mg/ml and 0.2 mg and treated with 10 mM TCEP (Thermo Sci, USA), spotted on the slide glass by 0.5 μl, specifically fixed to a sulfhydryl group for 1 hour, and then added with 100 mM 2-mercaptoethanol in 150 μl of a 2% BSA-TBS solution, thereby minimizing binding of the free aldehyde group and non-specific protein. 0.1 mg/ml human IgG (Erbitux) was dissolved in TBS and added by 100 μl per well to be bound with the protein G for 30 minutes and then a covalent bond therebetween was induced by irradiating UV for 30 minutes. As a control group, streptavidin was dissolved in PBS at concentrations of 1 mg/ml and 0.2 mg/ml and spotted by 0.5 μl. Next, 2% BSA was dissolved in 100 mM Tris-HCl, pH 7.5 and treated by 150 μl per well to remove the binding of the free aldehyde group and the non-specific protein. Each well was washed with TBST three times, a biotinylated human anti-EGFR antibody (Erbitux) was dissolved in 2% BSA-TBS at a concentration of 10 µg/ml, added by 100 µl per well, and stirred for 1 hour to be immobilized, and then washed with TBST. For antigen analysis, recombinant EGFR protein (Sino Biological Inc, China) was added in a human blood including 50 mM Tris-HCl (pH 7.5) at concentrations of 1, 0.05 and 0 µg/ml, respectively, and added with a FITC-labeled anti-EGFR-rat antibody (Abcam, USA) at a concentration of 1 µg/ml, added by 100 µl per well, and stirred for 1 hour. The respective wells were sequentially washed with TBS and TBST including 150 mM imidazole and then a fluorescence signal was analyzed in Ex488 nm/Em 515 nm through a slide glass fluorescent scanner.

As a result, as illustrated in FIG. 22, as compared with a streptavidin/biotin-antibody system or a pM-labeled 6H-2×PG4m/antibody system which is not irradiated with UV, in the pM-labeled 6H-2×PG4m/antibody system which is irradiated with UV, high sensitivity of at least five times was shown (see middle of FIG. 22) and the protein G was very useful in developing a biochip and a biosensor (see FIG. 22).

[Example 18] Verification of Availability in Cell Analysis in Blood of Protein Chip in which Antibody is Covalent-Bound with Protein G A highly oriented antibody may be used as a tool which is very useful even in analysis of the cancer cells in the blood sample of the bound protein chip. Accordingly, the analysis of the cancer cells in the blood sample was performed by covalent-binding a photoactivatable protein G on a slide glass and immobilizing the antibody to have high orientation by UV irradiation.

In detail, a maleide group was introduced on the surface of the protein G/antibody slide prepared by the method disclosed in Example 18, spotted with a 2×PG4m solution at a concentration of 1 mg/ml by 2 µl, immobilized for 1 hour, and immobilized to each well in a state in which anti-HER2 or EGFR human antibody was not irradiated with UV. Next, 10,000 of T67 cells expressing HER2 and A549 cells expressing EGFR were dispersed in 100 µl DMEM medium including 10% FBS and 10% human serum and added in the respective wells, and then stirred for 1 hour at a very slow speed. As a slide of a control group, 1 mg/ml streptavidin was spotted on an aldehyde slide by 2 µl and prepared. The slide was treated with the human serum and washed with PBS. Next, 10,000 A549 cells and 1.5 µg of a biotinylated anti-EGFR human antibody were simultaneously added in a medium solution and mixed for 30 minutes, and then divided in the wells coated with streptavidin by 100 µl, and stirred for 1 hour at a very slow speed. All the wells were washed two times with the DMEM medium including 10% FBS and then cells attached on the spotted region was analyzed.

As a result, as illustrated in FIG. 23, in the 6H-2×PG4m/antibody system irradiating the UV, anti-specific cell capturing was observed in the spotted region (see FIG. 23), in the 6H-2×PG4m/antibody system which is not irradiated with the UV or a streptavidin/biotin-antibody system, the anti-specific cell capturing was very low (the result was not shown), and thus it was verified that the photoactivatable protein G variant was very utilized for specific cell capturing in the blood (see FIG. 23).

In this specification, exemplary embodiments of the present invention have been classified into the first, second and third exemplary embodiments and described for conciseness. However, respective steps or functions of an exemplary embodiment may be combined with those of another exemplary embodiment to implement still another exemplary embodiment of the present invention.

The invention claimed is:

1. A protein G variant comprising an amino acid sequence in which:
   glutamine (Gln) at position 32,
   asparagine (Asn) at position 35, or
   aspartic acid (Asp) at position 40
is substituted by methionine (Met); or
   asparagine (Asn) at position 37
is substituted by arginine (Arg);
wherein the positions are counted from an N-terminal of any one amino acid sequence selected from the group consisting of:
   a first immunoglobulin G binding region C1 (PG-C1),
   a second immunoglobulin G binding region C2 (PG-C2), and
   a third immunoglobulin G binding region C3 (PG-C3)
of a protein G.

2. The protein G variant of claim 1, wherein the first immunoglobulin G binding region C1 (PG-C1) of the protein G is constituted by an amino acid sequence of SEQ ID NO: 2.

3. The protein G variant of claim 1, wherein the second immunoglobulin G binding region C2 (PG-C2) of the protein G is constituted by an amino acid sequence of SEQ ID NO: 3.

4. The protein G variant of claim 1, wherein the third immunoglobulin G binding region C3 (PG-C3) of the protein G is constituted by an amino acid sequence of SEQ ID NO: 4.

5. The protein G variant of claim 1, wherein one or two of the first immunoglobulin G binding region C1 (PG-C1), the second immunoglobulin G binding region C2 (PG-C2), or the third immunoglobulin G binding region C3 (PGC3) of the protein G are included.

6. A polynucleotide encoding the protein G variant of claim 1.

7. An expression vector including the polynucleotide of claim 6.

8. A pM-introduced protein G variant having photoactivity comprising an amino acid sequence in which
   glutamine at position 32,
   asparagine at position 35, or
   aspartic acid at position 40
is substituted by methionine; or
   asparagine at position 37 is substituted by arginine;
wherein the positions are counted from an N-terminal of any one amino acid sequence selected from a group consisting of:
   a first immunoglobulin G binding region C1 (PG-C1),
   a second immunoglobulin G binding region C2 (PG-C2), and
   a third immunoglobulin G binding region C3 (PG-C3)
of a protein G.

9. A method for preparing a protein G variant, the method comprising:
   substituting a methionine for
      glutamine at position 32,
      asparagine at position 35, or
      aspartic acid at position 40; or
   substituting an arginine for an asparagine at position 37;
   wherein the positions are counted from an N-terminal of any one amino acid sequence selected from the group consisting of:
   a first immunoglobulin G binding region C1 (PG-C1),
   a second immunoglobulin G binding region C2 (PG-C2), and
   a third immunoglobulin G binding region C3 (PG-C3)
of a protein G.

10. A method for preparing a pM-introduced protein G variant, the method comprising:
   a) preparing (i) an expression vector including the polynucleotide encoding the MRS variant comprising an amino sequence in which alanine at the position of 12th is substituted by glycine, leucine at the position 5 of 13th by serine, tyrosine at the position of 260th by phenylalanine, isoleucine at the position of 297th by valine, or histidine at the position of 301st by leucine from an N-terminus of a methionyl tRNA synthase (MRS) variant amino acid sequence of a wild-type *E. coli* MRS and (ii) the expression vector of claim 7;
   b) preparing a transformant by simultaneously introducing the expression vectors of the step a) into an *Escherichia coli* cell; and
   c) expressing a pM-labeled protein G variant by culturing the transformant of the step b).

11. A fusion protein in which an antibody is linked to the pM-introduced protein G variant of claim 8.

12. A biochip in which a highly oriented antibody is linked to the pM-introduced protein G variant of claim 8.

13. A biosensor in which a highly oriented antibody is linked to the pM-introduced protein G variant of claim 8.

14. A cell capturing system in which a highly oriented antibody linked to the pM-introduced protein G variant of claim 8.

15. A nanoparticle delivery system for antibody-labeled intravenous injection including an antibody linked to the protein G variant of claim 8 or a fragment thereof.

* * * * *